United States Patent
End et al.

(10) Patent No.: US 6,365,600 B1
(45) Date of Patent: Apr. 2, 2002

(54) (IMIDAZOL-5-YL)METHYL-2-QUINOLINONE DERIVATIVES AS INHIBITORS OF SMOOTH MUSCLE CELL PROLIFERATION

(75) Inventors: David William End, Ambler; Michael J. Zelesko, Hatboro, both of PA (US)

(73) Assignee: Janssen Pharmaceutica, N.V.

( * ) Notice: Subject to any disclaimer, the term of this patent is extended or adjusted under 35 U.S.C. 154(b) by 0 days.

(21) Appl. No.: 09/445,009

(22) PCT Filed: May 25, 1999

(86) PCT No.: PCT/EP98/03182

§ 371 Date: Nov. 30, 1999

§ 102(e) Date: Nov. 30, 1999

(87) PCT Pub. No.: WO98/55124

PCT Pub. Date: Dec. 10, 1998

Related U.S. Application Data

(60) Provisional application No. 60/047,376, filed on Jun. 2, 1997.

(51) Int. Cl.⁷ ............... A61K 31/47; A61K 31/165; A61K 31/170
(52) U.S. Cl. ............... 514/312; 514/154; 514/44
(58) Field of Search .................. 514/312, 154, 514/44

(56) References Cited

FOREIGN PATENT DOCUMENTS

| JP | H7-112930 | * | 5/1995 |
| WO | WO 97/16443 | * | 5/1997 |
| WO | WO 97 21701 |   | 6/1997 |

OTHER PUBLICATIONS

Nature Medicine, vol. 1, 1995, Indolfi Et Al.: "inhibition of cellular ras prevents smooth muscle cell proliferation after vascular injury in vivo"; pp 541–545.

Biochem. and Biophys. Res. Comm., vol. 202, No. 3, 1994, Irani Et Al.: "ras proteins regulate multiple mitogenic pathways in a10 vascular smooth muscle cells"; pp 1252–1258.

\* cited by examiner

Primary Examiner—Zohreh Fay
Assistant Examiner—Brian-Yong Kwon

(74) Attorney, Agent, or Firm—Myra McCormack

(57) ABSTRACT

This invention comprises the use of compounds of formula (I)

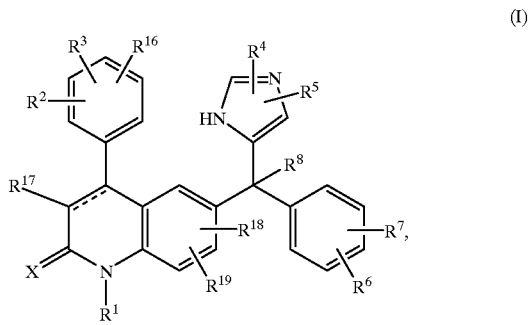

wherein the dotted line represents an optional bond; X is oxygen or sulfur; $R^1$ is hydrogen, $C_{1-12}$alkyl, $Ar^1$, $Ar^2C_{1-6}$alkyl, quinolinyl$C_{1-6}$alkyul, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula —Alk¹—C(=))—R⁹ or —Alk¹—S(O)₂—R⁹; $R^2$, $R^3$ and $R^{16}$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyloxy, mono- or di($C_{1-6}$alkyl)amino$C_{1-6}$alkyloxy, $Ar^1Ar^2C_{1-6}$alkyl, $Ar^2$-oxy, $Ar^2C_{1-6}$alkyloxy, hydroxycarbonyl, $C_{1-6}$alkyloxycarbonyl, trihalomethyl, trihalomethoxy, $C_{2-6}$alkenyl; $R^4$ and $R^5$ each independently are hydrogen, halo, $Ar^1$, $C_{1-6}$-alkyl, hydroxy$C_{1-6}$alkyl, $C_{1-6}$alkyloxy$C_{1-6}$alkyl, $C_{1-6}$alkyloxy, $C_{1-6}$alkylthio, amino, hydroxycarbony, $C_{1-6}$alkyloxycarbonyl, $C_{1-6}$alkylS(O)$C_{1-6}$alkul or $C_{1-6}$alkylS(O)₂$C_{1-6}$alkyl; $R^6$ and $R^7$ independenly are hydrogen, halo, cyano, $C_{1-6}$alkyl, 4,4-dimethyl-oxazolyl, $C_{1-6}$alkyloxy or $Ar^2$oxyl $R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxycarbonyl$C_{1-6}$alkyl, carboxy$C_{1-6}$alkyl, hydroxy$C_{1-6}$alkyl, amino$C_{1-6}$alkyl, mono- or di($C_{1-6}$alkyl)amino$C_{1-6}$alkyl, imidazolyl, halo$C_{1-6}$alkyl, $C_{1-6}$alkyloxy$C_{1-6}$alkyl, aminocarbonyl$C_{1-6}$alkyl, or a radical of formula —O—$R^{10}$, —S—$R^{10}$, —N—$R^{11}R^{12}$; $R^{17}$ is hydrogen, halo, cyano, $C_{1-6}$alkyl, $C_{106}$alkyloxycarbonyl, $Ar^1$; $R^{18}$ is hydrogen, $C_{1-6}$alkyl, $C_{1-6}$alkyloxy or halo; $R^{19}$ is hydrogen or $C_{1-6}$alkyl; for the manufacture of a medicament to inhibit smooth muscle cell proliferation.

8 Claims, No Drawings

(IMIDAZOL-5-YL)METHYL-2-QUINOLINONE DERIVATIVES AS INHIBITORS OF SMOOTH MUSCLE CELL PROLIFERATION

CROSS REFERENCE TO RELATED APPLICATIONS

This application is the national stage of application No. PCT/EP98/0312, filed May 25, 1998, which application claims priority from U.S. Provisional Application Ser. No. 60/047,376, filed Jun. 2, 1997.

FIELD OF THE INVENTION

The present invention is concerned with a method of use of compounds of formula (I) for the inhibition of smooth muscle cell proliferation.

BACKGROUND OF THE INVENTION

Proliferation of smooth muscle cells of the arterial wall in response to local injury is an important aetiologic factor of vascular proliferative disorders such as atheorsclerosis and restenosis after angioplasty. The incidence of restenosis after percutaneous transluminal coronary angioplasty (PTCA) has been reported to be as high as 45% within three to six months after PTCA treatment (Indolfi et al., *Nature medicine*, 1, 541–545 (1995)). Hence, compounds that inhibit smooth muscle cell proliferation can be very useful to prevent or treat vascular proliferative disorders such as atherosclerosis and restenosis.

Heparin is a well known compound to inhibit proliferation of smooth muscle cells after coronary angioplasty (Buchwald et al., *J. Cardiovasc. Pharmacol.*, 28,481–487 (1996)).

In out co-pending application PCT/EP96/04515, published on Jun. 19, 1997 as W)-97/21701, the compounds of formula (I), their preparation and compositions containing them are disclosed as farnesyl transferase inhibitors useful for the treatment of ras dependent tumors

DETAILED DESCRIPTION OF THE INVENTION

Unexpectedly, it has been found that the compounds of formula (I) can be used to inhibit smooth muscle cell proliferation. Consequently, the present invention relates to a method of use of compounds of formula (I) for treating vascular proliferative disorders in a warm-blooded animal.

The present invention relates to a method of use of compounds of formula (I)

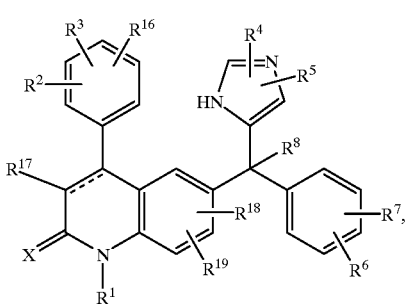

(I)

the pharmaceutically acceptable acid or base addition salts and the stereochemically isomeric forms thereof, wherein the dotted line represents an optional bond;

X is oxygen or sulfur;

$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di ($C_{1-6}$alkyl)amino$C_{1-6}$alkyl, amino$C_{1-6}$alkyl, or a radical of formula —$Alk^1$—C(=O)—$R^9$, —$Alk^1$—S(O)—$R^9$ or —$Alk^1$—S(O)$_2$—$R^9$, wherein $Alk^1$ is $C_{1-6}$alkanediyl, $R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;

$R^2R^3$ and $R^{16}$ each independently are hydrogen, hydroxy, halo, cyanao, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyloxy, mono- or di($C_{1-6}$alkyl)amino$C_{1-6}$alkyloxy, $Ar^1$, $Ar^2C_{1-6}$alkyl, $Ar^2$—oxy, $Ar^2C_{1-6}$alkyloxy, hydroxycarbonyl, $C_{1-6}$alkyloxycarbonyl, trihaalomethyl, trihalomethoxy, $C_{2-6}$alkenyl, 4,4-dimethyloxazolyl; or when on adjacent positions $R^2$ and $R^3$ taken together may form a bivalent radical of formula

 —O—$CH_2$—O— (a-1),

 —O—$CH_2$—$CH_2$—O— (a-2),

 —O—CH=CH— (a-3),

 —O—$CH_2$—$CH_2$— (a-4),

 —O—$CH_2$—$CH_2$—$CH_2$— (a-5), or

 —CH=CH—CH=CH— (a-6);

$R^4$ and $R^5$ each independently are hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2C_{1-6}$alkyl;

$R^6$ and $R^7$ each independently are hydrogen, halo, cyano, $C_{1-6}$alkyl, $C_{1-6}$alkyloxy, $Ar^2$-oxy, trihalomethyl, $C_{1-6}$alkylthio, di($C_{1-6}$alkyl)amino, or when on adjacent positions $R^6$ and $R^7$ taken together may form a bivalent radical of formula

 —O—$CH_2$—O— (c-1), or

 —C=CH—CH=CH— (c-2);

$R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxycarbonyl$C_{1-6}$alkyl, carboxy$C_{1-6}$alkyl, hydroxy$C_{1-6}$alkyl, amino$C_{1-6}$alkyl, mono- or di($C_{1-6}$alkyl)amino$C_{1-6}$alkyl, imidazoly, halo$C_{1-6}$alkyl, $C_{1-6}$alkyl, $C_{1-6}$alkyloxy$C_{1-6}$alkyl, aminocarbonyl$C_{1-6}$alkyl, or a radical of formula

 —O—$R^{10}$ (b-1),

 —S—$R^{10}$ (b-2),

 —N—$R^{11}R^{12}$ (b-3), wherein $R^{10}$ is hydrogen, $C_{1-6}$alkyl, $C_{1-6}$alkylcarbonyl, $Ar^1$, $Ar^2C_{1-6}$alkyl, $C_{1-6}$alkyloxycarbonyl$C_{1-6}$alkyl, or a radical or formula —$Alk^2$—$OR^{13}$ or —$Alk^2$—$NR^{14}R^{15}$;

$R^{11}$ is hydrogen, $C_{1-12}$alkyl, $Ar^1$ or $Ar^2C_{1-6}$alkyl;

$R^{12}$ is hydrogen, $C_{1-6}$alkyl, $C_{1-6}$alkylcarbonyl, $C_{1-6}$alkylcarbonyl, $C_{1-6}$alkylaminocarbonyl, $Ar^1$, $Ar^2C_{1-6}$alkyl, $C_{1-6}$alkylcarbonyl$C_{1-6}$alkyl, a natural amino acid, $Ar^1$carbonyl, $Ar^2C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $c_{1-6}$alkylcarbonylamino, or a radical or formula —Alk$^2$—OR$^{13}$ or —Alk$^2$—NR$^{14}$R$^{15}$;

wherein Alk$^2$ is $C_{1-6}$alkanediyl;

$R^{13}$ is hydrogen, $C_{1-6}$alkyl;. $C_{1-6}$alkylcarbonyl, hydroxy$C_{1-6}$alkyl, $Ar^1$ or $AR^2C_{1-6}$alkyl;

$R^{14}$ is hydrogen, $C_{1-6}$alkyl, $Ar^1$ $Ar^2C_{1-6}$alkyl;

$R^{15}$ is hydrogen, $C_{1-6}$alkyl, $C_{1-6}$alkylcarbonyl, $Ar^1$ or $Ar^2C_{1-6}$alkyl;

$R^{17}$ is hydrogen, halo, cyano, $C_{1-6}$alkyl, $C_{1-6}$alkyloxycarbonyl, $Ar^1$;

$R^{18}$ is hydrogen, $C_{1-6}$alkyl, $C_{1-6}$alkyloxy or halo;

$R^{19}$ is hydrogen or $C_{1-6}$alkyl;

$Ar^1$ is phenyl or phenyl substituted with $C_{1-6}$alkyl, hydroxy, amino, $C_{1-6}$alkyloxy or halo; and $Ar^2$ is phenyl or phenyl substituted with $C_{1-6}$alkyl, hydroxy, amino, $C_{1-6}$alkyloxy or halo; for the inhibition of smooth muscle cell proliferation.

$R^4$ or $R^5$ may also be bound to one of the nitrogen atoms in the imidazole ring. In that case the hydrogen on the nitrogen is replaced by $R^4$ and $R^5$ and the meaning of $R^4$ and $R^5$ when bound to the nitrogen is limited to hydrogen, $Ar^1$, $C_{1-6}$alkyl, hydroxy-$C_{1-6}$alkyl, $C_{1-6}$alkyloxy$C_{1-6}$alkyl, $C_{1-6}$alkyloxycarbonyl, $C_{1-6}$alkylS(O)$C_{1-6}$alkyl, $C_{1-6}$alkylS(O)$_2C_{1-6}$alkyl.

As used in the foregoing definitions and hereinafter halo defines fluro, chloro, bromo and iodo; $C_{1-6}$alkyl defines straight and branched chained saturated hydrocarbon radicals having from 1 to 6 carbon atoms such as, for example, methyl, ethyl, propyl, butyl, pentyl, hexyl and the like; $C_{1-8}$alkyl encompasses the straight and branched chained saturated hydrocarbon radicals as defined in $C_{1-6}$alkyl as well as the higher homologues thereof containing 7 or 8 carbon atoms such as, for example heptyl or octyl; $C_{1-12}$alkyl again encompasses $C_{1-8}$alkyl and the higher homologues thereof containing 9 to 12 carbon atoms, such as, for example, nonyl, decyl, undecyl, dodecyl; $C_{1-16}$alkyl again encompasses $C_{1-12}$alkyl and the higher homologues thereof containing 13 to 16 carbon atoms, such as, for example tridecyl, tetradecyl, pentedecyl and hexadecyl; $C_{2-6}$alkenyl defines straight and branded chain hydrocarbon radicals containing one double bond and having from 2 to 6 carbon atoms such as, for example, ethylyl, 2-propenyl, 3-butenyl, 2-pentenyl, 3-pentenyl, 3-methyl-2-butenyl, and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof. The term "C(=O)" refers to a carbonyl group, "S(O)" refers to a sulfoxide and "S(O)$_2$" to a sulfon. The term "natural amino acid" refers to a natural amino acid that is bound via a covalent amide linkage formed by loss of a molecule of water between the carboxyl group of the amino acid and the amino group of the remainder of the molecule. Examples of natural amino acids are glycine, alanine, valine, leucine, isoleucine, methionine, proline, phenylanaline, tryptophan, serine, threonine, cycsteine, tyrosine, asparagine, glutamine, aspartic acid, glutamic acid, lysine, arginine, histidine.

The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula )I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formula (I) are able to form. Examples of such forms are e.g. hydrates, alcoholates and the like.

The term steroechemically isomeric forms of compounds of formula (I), as used hereinabove, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible sterochemically isomeric forms which said compound may possess. Said mixture may contain all diasteromers and/or enantiomers of the basic molecular structure of said compound. All sterochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable acid or base addition salts and all steroisomeric forms.

Preferably the substitutent $R^{18}$ is situated on the 5 or 7 position of the quinolinone moiety and substituent $R^{19}$ is situated on the 8 position when $R^{18}$ is on the 7-position.

Interesting compounds are those compounds of formula (I) wherein X is oxygen.

Also interesting compounds are those compounds of formula (I) wherein the dotted line represents a bond, so as to form a double bond.

Another group of interesting compounds are those compounds of formula (I) wherein $R^1$ is hydrogen, $C_{1-6}$alkyl, $C_{1-6}$alkyloxy$C_{1-6}$alkyl, di ($C_{1-6}$alkyl)amino$C_{1-6}$alkyl, or a radical of formula —Alk$^1$ —C(=O)—R$^9$, wherein Alk$^1$ is methylene and $R^9$ is $C_{1-8}$alkylamino substituted with $C_{1-6}$alkyloxycarbonyl.

Still another group of interesting compounds are those compounds of formula (I) wherein $R^3$ is hydrogen or halo; and $R^2$ is halo, $C_{1-6}$alkyl, $C_{2-6}$alkenyl, $C_{1-6}$alkyloxy, trihalomethoxy or hydroxy$C_{1-6}$alkyloxy.

A further group of interesting compounds are those compounds of formula (I) wherein $R^2$ and $R^3$ are on adjacent positions and taken together to form a bivalent radical of formula (a-1), a-2) or (a-3).

A still further group of interesting compounds are those compounds of formula (I) wherein $R^5$ is hydrogen and $R^4$ is hydrogen or $C_{1-6}$alkyl.

Yet another group of interesting compounds are those compounds of formula (I) wherein $R^7$ is hydrogen; and $R^6$ is $C_{1-6}$alkyl or halo, preferably chloro, especially 4-chloro.

A particular group of compounds are those compounds of formula (I) wherein $R^8$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, imidazolyl, or a radical of formula —$NR^{11}R^{12}$ wherein $R^{11}$ is hydrogen or $C_{1-12}$alkyl and $R^{12}$ is hydrogen, $C_{1-6}$alkyl, $C_{1-6}$alkyloxy, hydroxy, $C_{1-6}$alkyloxy$C_{1-6}$alkylcarbonyl, or a radical of formula —Alk$^2$—OR$^{13}$ wherein $R^{13}$ is hydrogen or $C_{1-6}$alkyl.

Preferred compounds are those compounds wherein $R^1$ is hydrogen, $C_{1-6}$alkyl, $C_{1-6}$alkyloxy$C_{1-6}$alkyl, di($C_{1-6}$akyl)amino$C_{1-6}$alkyl, or a radical of formula —Alk$^1$—C(=))—$R^9$, wherein Alk$^1$ is methylene and $R^9$ is $C_{1-8}$alkylamino substituted with $C_{1-6}$alkyloxycarbonyl; $R^2$ is halo, $c_{1-6}$alkyl, $C_{2-6}$alkenyl, $C_{1-6}$alkyloxy, trihalmethoxy, hydroxy$C_{1-6}$alkyloxy or Ar$^1$; $R^3$ is hydrogen; $R^4$ is methyl bound to the nitrogen in 3-position of the imidazole; $R^5$ is hydrogen; $R^6$ is chloro; $R^7$ is hydrogen; $R^8$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, imidazolyl, or a radical of formula —$NR^{11}R^{12}$ wherein $R^{11}$ is hydrogen or $C_{1-12}$alkyl and $R^{12}$ is hydrogen, $C_{1-6}$alkyl, $C_{1-6}$alkyloxy, $C_{1-6}$alkyloxy$C_{1-6}$alkylcarbonyl, or a radical of formula —Alk$^2$—OR$^{13}$ wherein $R^{13}$ is $C_{1-6}$alkyl; $R^{17}$ hydrogen and $R^{18}$ is hydrogen.

Most preferred compounds are
4-(3-chlorophenyl)-6-[(4-chlorophenyl)hydroxy(1-methyl-1H-imidazol-5-yl)methyl]-1-methyl-2(1H)-quinolinone,
6-[amino(4-chlorophenyl)-1-methyl-1H-imidazol-5-ylmethyl]-4-(3-chlorophenyl)-1-methyl-2(1H)-quinolinone;
6-[(4-chlorphenyl)hydroxy(1-methyl-1H-imidazol-5-yl) methyl]-4(3-ethyoxyphenyl)-1-methyl-2(1H)-quinolinone;
6[(4-chlorophenyl)(1-methyl-1H-imidazol-5-yl)methyl]-4 (3-ethoxyphenyl)-1-methyl-2(1H)-quinolinone monohydrochloride.monohydrate;
6[amino(4-chlorophenyl)(1-methyl-1H-imidazol-5yl) methyl]-4(3-ethoxyphenyl)-1-methyl-2-(1H)-quinolinone,
6[amino(4-chlorophenyl)(1-methyl-1H-imidazol-5yl) methyl]-1methyl-4-(3-propylphenyl)-2(1H)-quinolinone; a stereoisomeric form thereof or a pharmaceutically acceptable acid or base addition salt; and
(+)-6-[amino(4-chlorophenyl)(1-methyl-1H-imidazol-5-yl) methyl]-4-(3-chlorophenyl)-1-methyl-2-(1H)-quinolinone; or a pharmaceutically acceptable acid addition salt thereof.

The compounds of formula (I), wherein X is oxygen, said compounds being represented by formula (I-a), may be prepared by hydrolysing an intermediate ether of formula (II), wherein R is $C_{1-6}$alkyl, according to art-known methods, such as stirring the intermediate of formula (II) in an aqueous acid solution. An appropriate acid is for instance hydrochloric acid. Subsequently the resulting quinolinone wherein $R^1$ is hydrogen may be transformed into a quinolinone, wherein $R^1$ has a meaning as defined hereinabove apart from hydrogen, by art-known N-alkylation.

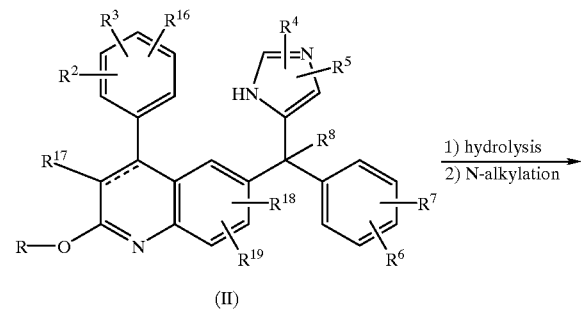

(II)

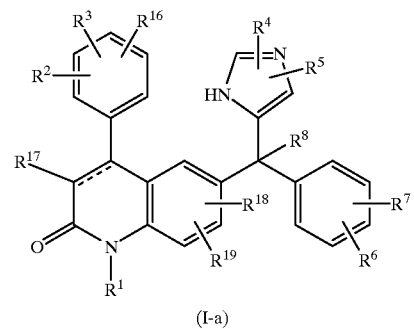

(I-a)

The compounds of formula (I), wherein $R^8$ is hydroxy, said compound being referred to as compound of formula (I-b) may be prepared by reacting an intermediate ketone of formula (III) with a intermediate of formula (IV-a), wherein P is an optional protective group such as, for example, a sulfonyl group, e.g. a dimethylamino sulfonyl group, which can be removed after the addition reaction. Said reaction requires the presence of a suitable strong base, such as, for example, butyl lithium in an appropriate solvent, such as, for example, tetrahydrofuran and the presence an appropriate silanederivative, such as, for example, triethylchlorosilane. During the work-up procedure an intermediate silane derivative is hydrolyzed. Other procedures with protective groups analogous to silanederivatives can also be applied.

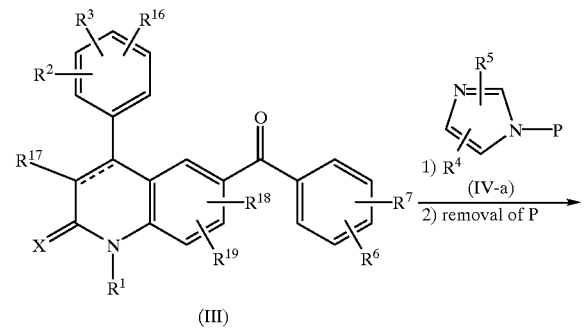

(III)

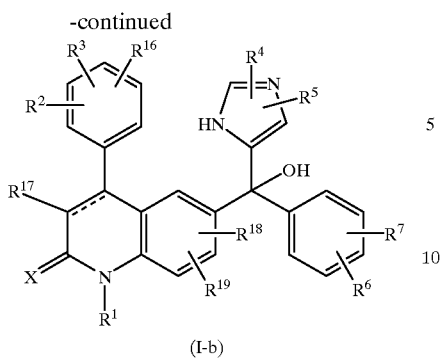

(I-b)

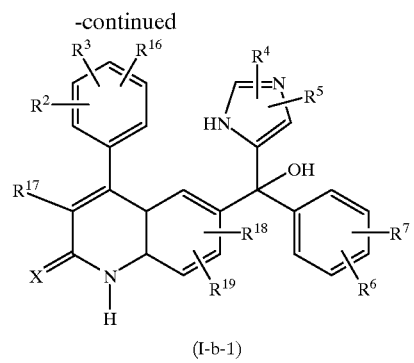

(I-b-1)

Compounds of formula (I-b-1), being compounds of formula (I-b) wherein the dotted line is a bond and $R^1$ is hydrogen, can be prepared by reacting an intermediate of formula (XXI) with an intermediate of formula (IV-a), as described hereinabove for the synthesis of compounds of formula (I-b). The thus obtained intermediate of formula (XXII) undergoes ring opening of the isoxazole moiety by stirring it with an acid, such as, e.g. $TiCl_3$, in the presence of water. Subsequent treatment of an intermediate of formula (XXIII) with a suitable reagent such as, e.g. $R^{17}CH_2COCl$ or $R^{17}CH_2COOC_2H_5$, yields either directly a compound of formula (I-B-1) or an intermediate which can be converted to a compound of formula (I-b-1) by treatment with a base such as, e.g. potassium ter-butoxide.

Intermediates of formula (XXI) can conveniently be prepared by treating an intermediate of formula (XVI), described hereinafter, under acidic conditions.

Compounds of formula (I0) wherein $R^8$ is a radical of formula $-N-R^{11}R^{12}$, said compounds being represented by formula (I-g) may be prepared by reacting an intermediate of formula (XIII), wherein W is an appropriate leaving group such as, for example, halo, with a reagent of formula (XIV). Said reaction may be performed by stirring the reactants in an appropriate solvent such as, for example, tetrahydrofuran.

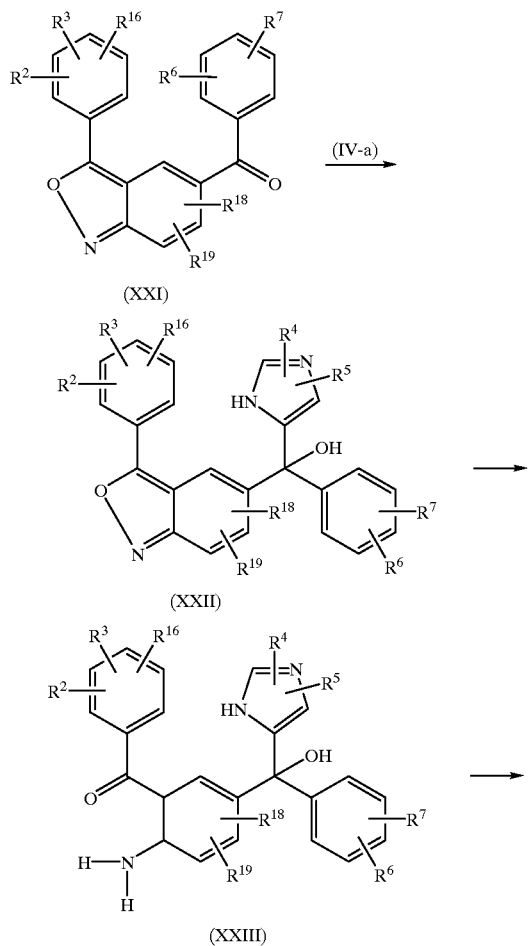

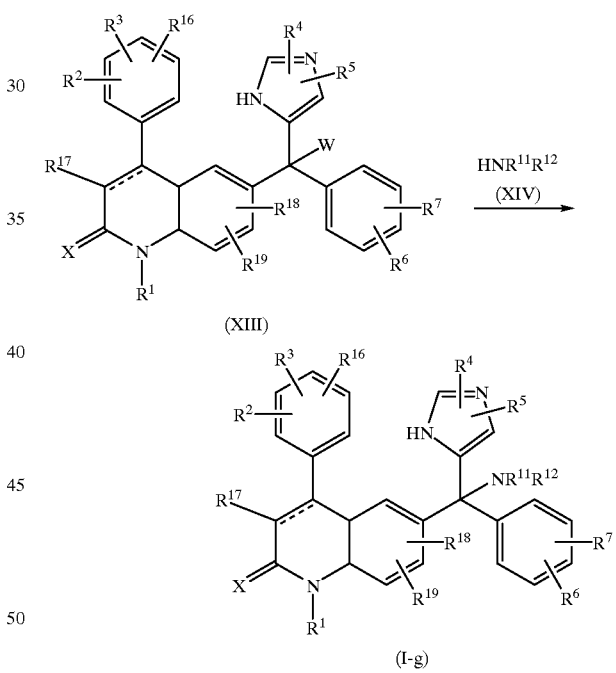

The compounds of formula (I) may also be prepared by converting compounds of formula (I) into other compounds of formula (I).

Compounds wherein the dotted line represents a bond can be converted into compounds wherein the dotted lines does not represent a bond, by art-known hyudrogenation methods. Vice versa, compounds wherein the dotted liens does not represent a bond may be converted into compounds wherein the dotted line represents a bond by art-known oxidation reactions Compounds of formula (I) wherein $R^8$ is hydroxy, said compounds being represented by formula (I-b) may be converted into compounds of formula (I-c), wherein $R^{8a}$ has the meaning of $R^{10}$ except for hydrogen, by art-know O-alkylation or O-acylation reactions, such as, for instance, reacting the compound of formula (I-b) with an alkylating reagent such as $R^{8a}$—W in appropriate conditions, such as, for example, a dipolar aprotic solvent, e.g. DMF, in the presence of a base, e.g. sodium hydride. W is a suitable leave group, such as, for example, halo or a sulfonyl group.

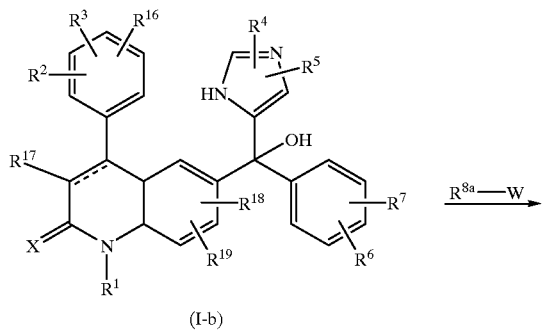

(I-b)

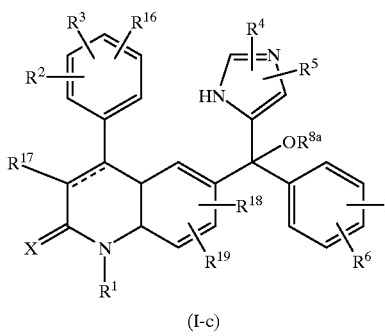

(I-c)

As an alternative to the above reaction procedure, compounds of formula (I-c) may also be prepared by reacting an intermediate of formula (I-b) with a reagent of formula $R^{8a}$—OH in acidic medium.

Compounds of formula (I-b) may also be converted into compounds of formula (I-g), wherein $R^{11}$ is hydrogen and $R^{12}$ is $C_{1-16}$alkylcarbonyl, by reacting compounds of formula (I-b) in acidic medium, such as sulfuric acid, with $C_{1-16}$alkyl—CN in a Ritter type reaction. Further, compounds of formula (I-b) may also be converted into compounds of formula (I-g), wherein $R^{11}$ and $R^{12}$ are hydrogen, by reacting compounds (I-b) with ammonium acetate and subsequent treatment with $NH_3$ (aq.).

Compounds of formula (I-b) may also be converted into compounds of formula (I-d), wherein $R^8$ is hydrogen, by submitting the compounds of formula (I-b) to appropriate reducing conditions, such as, stirring in trifluoroacetic acid in the presence of an appropriate reducing agent, such as sodium borohydride or alternatively stirring the compounds of formula (I-b) in acetic acid in the presence of formamide. Furthermore, compounds of formula (I-d) wherein $R^8$ is hydrogen may be converted into compounds of formula (I-e) wherein $R^{8b}$ is $C_{1-6}$alkyl by reacting compounds of formula (I-d) with a reagent of formula (V) in an appropriate solvent, such as, for instance, diglyme in the presence of a base such as, for example, potassium butoxide.

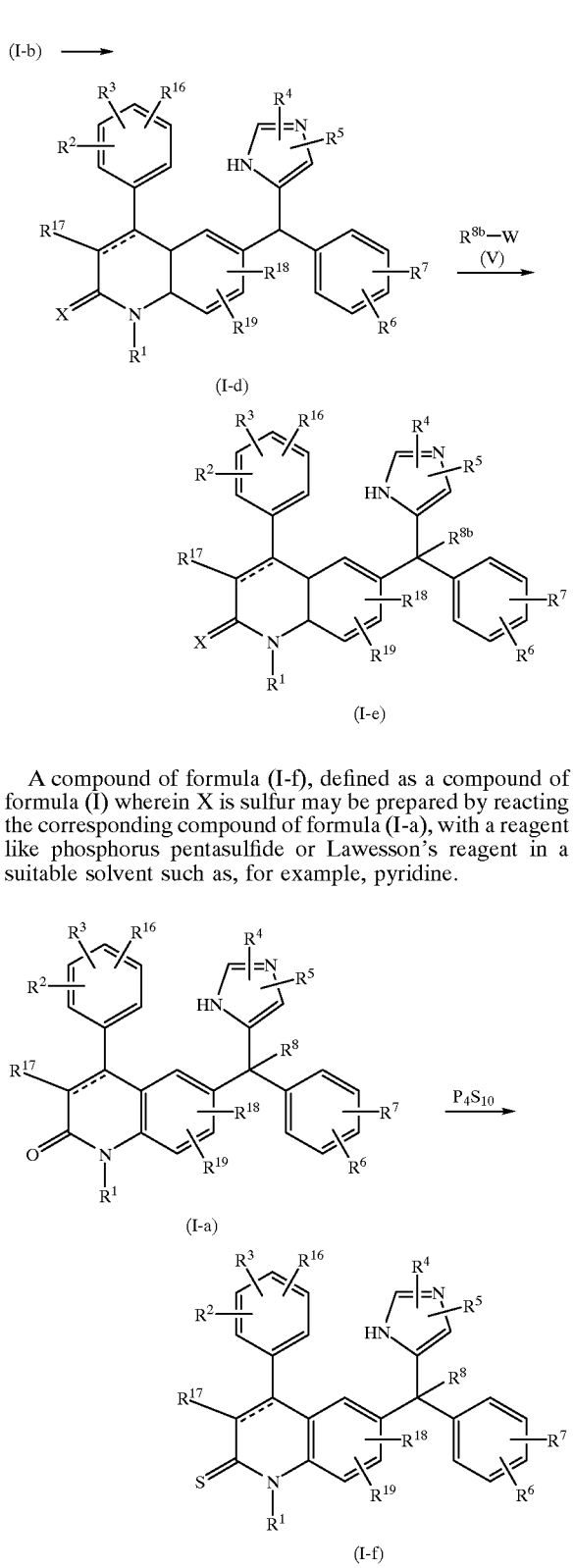

A compound of formula (I-f), defined as a compound of formula (I) wherein X is sulfur may be prepared by reacting the corresponding compound of formula (I-a), with a reagent like phosphorus pentasulfide or Lawesson's reagent in a suitable solvent such as, for example, pyridine.

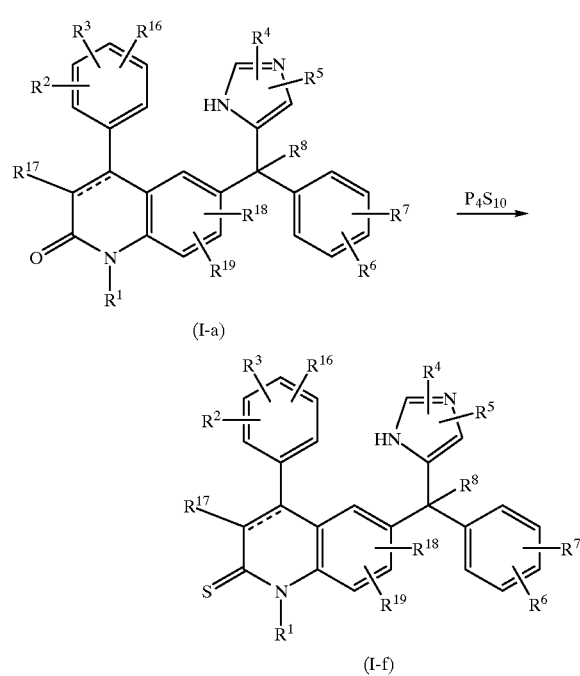

Compounds of formula of formula (I), wherein $R^1$ is hydrogen and X is oxygen, said compounds being defined as compounds of formula (I-a-1) may be prepared by reacting a nitrone of formula (VI) with the anhydride of a carboxylic acid, such as, for example, acetic anhydride, thus forming the corresponding ester on the 2 position of the quinoline moiety. Said quinoline ester can be hydrolyzed in situ to the corresponding quinolinone using a base such as, for example, potassium carbonate.

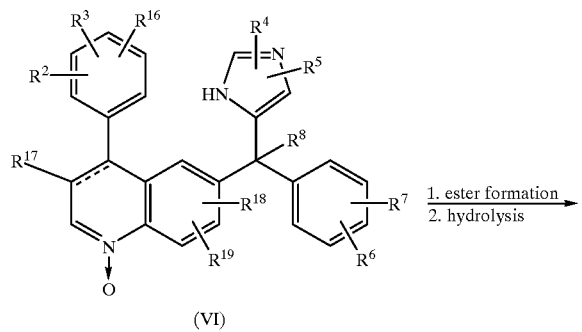

(VI)

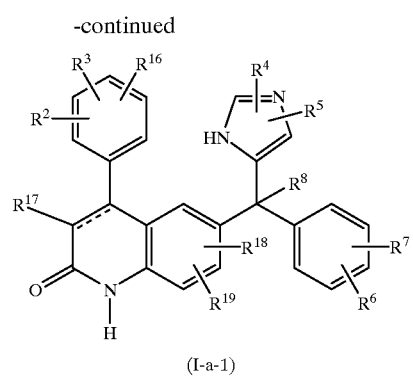

(I-a-1)

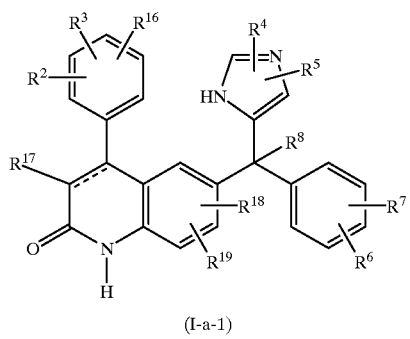

(I-a-1)

Alternatively, compounds of formula (I-a-1) can be prepared by reacting a nitrone of formula (VI) with a sulfonyl containing electrophilic reagent such as, for example, p-toluenesulfonylchloride in the presence of a base such as, for example, aqueous potassium carbonate. The reaction initially involves the formation of a 2-hydroxy-quinoline derivative which is subsequently tautomerized to the desired quinolinone derivative. The application of art-known conditions of phase transfer catalysis may enhance the rate of the reaction.

Compounds of formula (I-a-1) may also be prepared by an intramolecular photochemical rearrangement of compounds of formula (VI). Said rearrangement can be carried out by dissolving the reagents in a reaction-inert solvent and irradiating at a wavelength of 366 nm. It is advantageous to use degassed solutions and to conduct the reaction under an inert atmosphere such as, for example, oxygen free argon or nitrogen gas, in order to minimize undesired side reactions or reduction of quantum yield.

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond.

Intermediates of formula (III) may be prepared by reacting a quinolinone derivative of formula (VIII) with an intermediate of formula (IX) or a functional derivative thereof under appropriate conditions, such as, for example, a strong acid, e.g. polyphosphoric acid in an appropriate solvent. The intermediate of formula (VIII) may be formed by cyclization of an intermediate of formula (VII) by stirring in the presence of a strong acid, e.g. polypohsphoric acid. Optionally said cyclization reaction may be followed by an oxidation step, which can be performed by stirring the intermediate formed after cyclization in an appropriate solvent, such as, for example, a halogenated aromatic solvent, e.g. bromobenzene, in the presence of a oxidizing agent, e.g. bromine or iodine. At this stage it may be appropriate to change the $R^1$ substituent by art-known functional group transformation reaction.

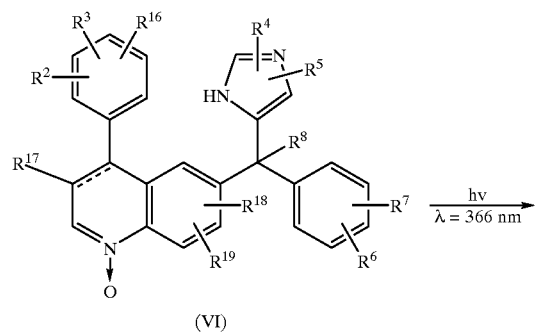

(VI)

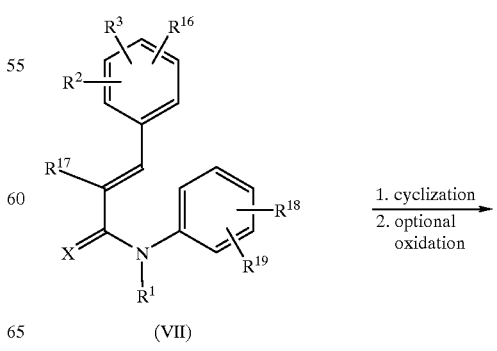

(VII)

-continued

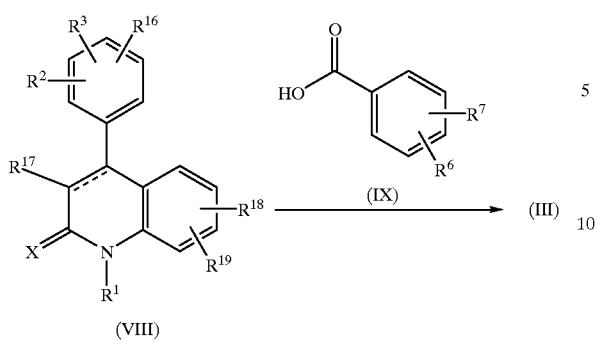 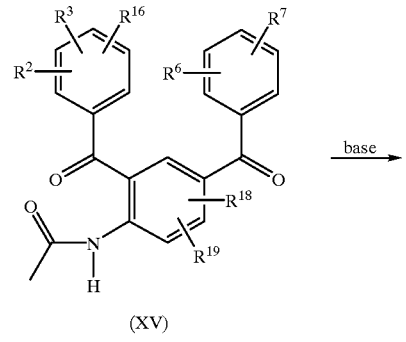

Intermediates of formula (III-a-1), being intermediates of formula (III) wherein the dotted line is a bond, $R^1$ and $R^{17}$ are hydrogen and X is oxygen, can be prepared starting from an intermediate of formula (XVII), which is conveniently prepared by protecting the corresponding ketone. Said intermediate of formula (XVII) is stirred with an intermediate of formula (XVIII) in the presence of a base such as sodium hydroxide, in an appropriate solvent, such as an alcohol, e.g. methanol. The thus obtained intermediate of formula (XVI) undergoes hydrolysis of the ketan and ring opening of the isoxazole moiety by stirring the intermediate of formula (VXI) with an acid, such as for example, $TiCl_3$, in the presence of water. Subsequently acidic anhydride is used to prepare an intermediate of formula (XV), which undergoes ring closure in the presence of a base such as, for example, potassium tert-butoxide.

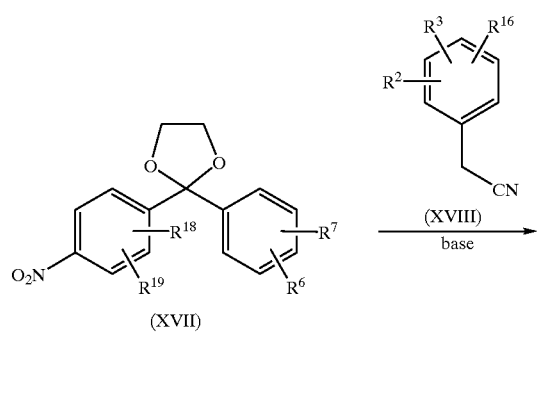

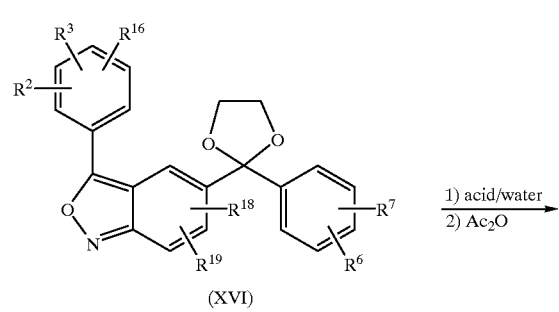

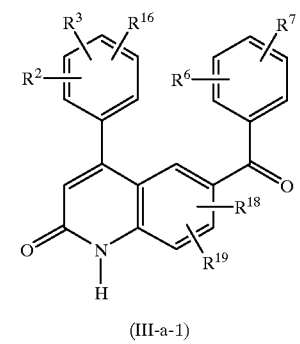

Intermediates of formula (III-a-1) can easily be converted to intermediates of formula (III-a), defined as intermediates of formula (III) wherein the dotted line represents a bond, X is oxygen, $R^{17}$ is hydrogen and $R^1$ is other than hydrogen, using art-known N-alkylation procedures.

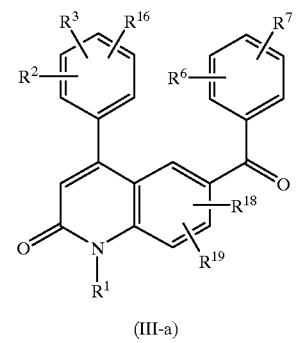

An alternative way to prepare intermediates of formula (III-a-1), wherein X is oxygen and $R^1$ is hydrogen, starts from an intermediate of formula (VXI), which is conveniently converted to intermediates of formula (XIX) using catalytic hydrogenation conditions, e.g. by using hydrogen gas and palladium on carbon in a reaction-inert solvent such as, e.g. tetrahydrofuran. Intermediates of formula (XIX) are converted to intermediates of formula (XX) by submitting intermediates (XIX) to an acetylation reaction, e.g. by treatment with the anhydride of a carboxylic acid, e.g. acetic anhydride in a reaction-inert solvent, e.g. toluene, and subsequent treatment with a base such as, e.g. potassium tert-butoxide in a reaction-inert solvent, e.g. 1,2-dimethoxyethane. Intermediates of formula (III-a-1) can be obtained by treating intermediates of formula (XX) in acidic conditions.

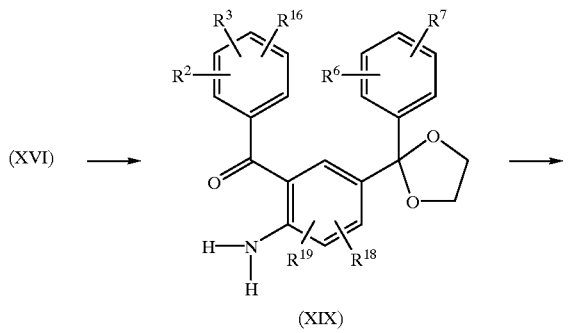

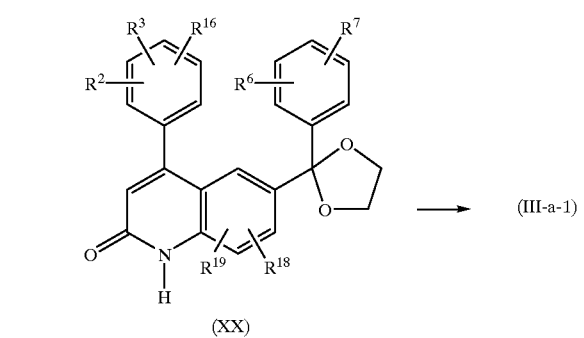

Intermediates of formula (II) may be prepared by reacting an intermediate of formula (X), wherein W is an appropriate leaving group, such as, for example, halo, with an intermediate ketone of formula (XI). This reaction is performed by converting the intermediate of formula (X) into a organometallic compound, by stirring it with a strong base such as butyl lithium and subsequently adding the intermediate ketone of formula (XI). Although this reaction gives a first instance a hydroxy derivative (i.e. $R^8$ is hydroxy), said hydroxy derivative can be converted into other intermediates wherein $R^8$ has another definition by performing art-known (functional group) transformations.

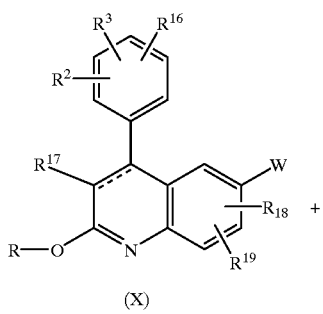

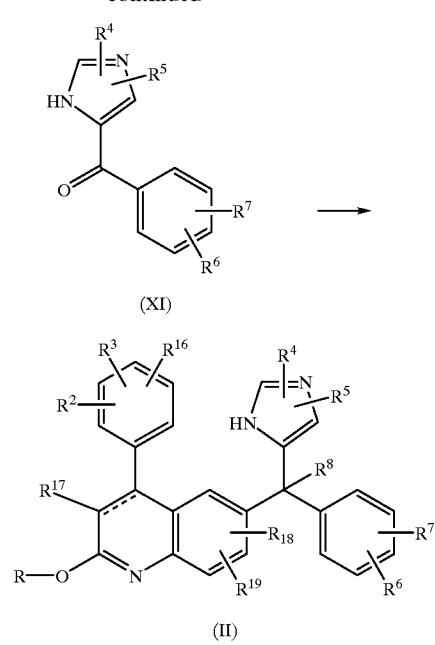

The intermediate nitrones of formula (VI) may be prepared by N-oxidizing quinoline derivatives of formula (XII) with an appropriate oxidizing agent such as, for example, m-chloro-peroxybenzoic acid or $H_2O_2$ in an appropriate solvent such as, for example, dichloromethane.

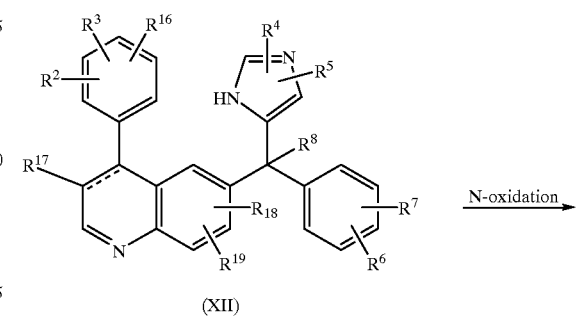

Said N-oxidation may also be carried out on a precursor of a quinoline of formula (XII).

The intermediates of formula (XII) are supposed to be metabolized in vivo into compounds of formula (I) via intermediates of formula (VI). Hence, intermediates of formula (XII) and (VI) may act as prodrugs of compounds of formula (I).

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enamtiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

This invention provides a method of use of compounds of formula (I) to inhibit the proliferation of smooth muscle cells, as illustrated by pharmacological example C.1.

Hence, the compounds of formula (I) can be used for the manufacture of a medicament for the inhibition of smooth muscle cell proliferation and consequently the use for the manufacture of a medicament for the treatment of vascular proliferative disorders such as atherosclerosis and restenosis is also provided.

It has been proposed in literature that the mechanism behind smooth muscle cell proliferation involves the loss of normal regulation of cellular growth, a process wherein ras proteins plays a significant role. Accordingly, it has been suggested that compounds having farnesyl transferase inhibiting properties, can be useful to prevent smooth muscle cell proliferation after vascular injury (Indolfi et al., *Nature medicine*, 1, 541–545 (1995) and Irani et al., *Biochemical and biophysical research Communications*, 202, 1252–1258, (1994)).

A therosclerosis is a disorder characterized by the deposition of fatty substances in and fibrosis of the inner layer of the arteries.

Restenosis is the narrowing of tubular passageways of a subject after the tubular walls have been traumatized. This can be caused by uncontrolled cellular proliferation of neointimal tissue which often is a complication due to the use of revascularization techniques such as, e.g. saphenous vein bypass grafting, endarterectomy, percutaneous transluminal coronary angioplaty (PTCA) and the like. Restenosis refers to a worsening or recurrence of lumenal stenosis in an artery which is characterized by a hyperplasia of cells of the arterial wall. In this respect, restenosis differs notably from an occlusion of the artery by an arterial atherosclerotic plaque or occlusion by thrombus.

Restenosis is not restricted or limited to the coronary arteries. It can also occur in for example peripheral vascular systems.

Angioplasty is a technique whereby an artery clogged by an atherosclerotic plaque and/or thrombus is mechanically cleared. Such a clogged or blocked artery prevents adequate blood flow. Angioplasty procedures are much less invasive and much less traumatic than conventional alternatives such as coronary bypass surgery and have gained widespread acceptance as a means of obtaining dilation or clearance of arteries. In conventional angioplasty procedures, a small balloon-tipped catheter is introduced into an artery, often using a guide wire or a catheter tube in which a collapsed balloon may be positioned at one more point of arterial stenosis, i.e. narrowing. Once positioned within the blockage, the balloon is inflated, thereby stretching and/or fracturing the blockage and enlarging the lumen (opening) of the artery. After the balloon is deflated and removed from the artery, the artery's internal diameter is generally larger, resulting in restoration of blood flow. These balloon and catheter assemblies are often referred to as coronary balloon dilation catheters. However, said angioplaty procedures involve risk of both local and systemic thromboembolic effects, tearing of an arterial wall and restenosis.

Restenosis after balloon angioplasty is also referred to as 'percutaneous transluminal coronary angioplasty restenosis' and is characterized by the return of blockage in the artery due to neointimal formation of a layer of smooth muscle cells in the intima after balloon injury.

Accordingly, the present invention provides a method of treating vascular proliferative disorders in a warm-blooded animal, such as atherosclerosis or restenosis, which comprises administering to said warm-blooded animal a prophylactically or therapeutically effective amount of a compound of formula (I).

The present invention provides further a method of inhibiting smooth muscle cell proliferation in a warm-blooded animal which comprises administering to said warm-blooded animal a prophylactically or therapeutically effective amount of a compound of formula (I).

Balloon angioplasty can be followed by a mechanical/surgical procedure known as intravascular stenting, a procedure in which an expandable metallic sleeve, or scaffold, i.e. a stent, is placed within the artery after angioplasty. However, after the insertion of the stent a disorder known as 'coronary artery stent restenosis' can occur whereby the blockage in the artery returns due to neointimal formation of a layer of smooth muscle cells in the intima. Therefore, it may be advantageous to cover or coat said stent with a coating material which comprises a compounds of formula (I) in order to inhibit smooth muscle cells proliferation. Hence, in an aspect, this invention also provides stents covered or coated with a coating material which comprises an amount of a compound of formula (I) effective in preparing, treating or reducing smooth muscle cell proliferation. Commercially available stents are e.g. balloon expandable stents such as, e.g. Palmaz-Schatz™ stent, Strecker™ stent and Gianturco-roubin™ stent, and self expandable stents such as, e.g. Gianturco™ expandable wire stent and Wallstent™, other stents are Palmaz-Schatz Crown™, Cross-Flex™, ACS Multi-Link™, Nir™, Micro Stent II™ and Wiktor™.

In a way, the invention also relates to catheters, or other transluminal devices coated or covered with a coating material which comprises an amount of a compound of formula (I) effective in preventing, treating or reducing smooth muscle cell proliferation.

The metallic surface of a stent can be coated in a number of ways. The surface can be prepared by a two-step procedure including covalently linking an organosilane having amine reactive sites, with the surface of the metallic member, typically through a metal oxide thereof. Also, an organosilane having a vinyl functionality pendant from the surface can be used. Thereafter, a biocompatible coating material can be covalently linked to the organosilane coating.

The coating layer comprising an amount of a compound of formula (I) may also be applied as a mixture of a polymeric precursor and a compound of formula (I) which is finely divided or dissolved in a polymer solvent or vehicle which is thereafter cured in situ.

The coating may be applied by dipping or spraying using evaporative solvent materials of relatively high vapor pressure to produce the desired viscosity and coating thickness. The coating further is one which adheringly conforms to the surface of the filaments of the open structure of the stent so that the open lattice nature of the structure of the braid or other pattern is preserved in the coated device.

The major constituent of the stent coating should have elastomeric properties. The stent coating is preferably a suitable hydrophobic biostable elastomeric material which does not degrade and which minimizes tissue rejection and tissue inflammation and one which will undergo encapsulation by tissue adjacent the stent implantation site. Polymers suitable for such coatings include silicones (e.g. polysiloxanes and substituted polysiloxanes), polyurethanes, thermoplastic elastomers in general, ethylene vinyl acetate copolymers, polyolefin elastomers, and EPDM rubbers.

The loading of the stent coating with the compound of formula (I) may vary. The desired release rate profile can be tailored by varying the coating thickness, the radial distribution, the mixing method, the amount of said compound of formula (I), and the crosslink density of the polymeric material.

Methods for coating stents are described in, e.g., WO-96/32907, U.S. Pat. No. 5,607,475, U.S. Pat. No. 5,356,433, U.S. Pat. No. 5,213,898, U.S. Pat. No. 5,049,403, U.S. Pat. No. 4,807,784 and U.S. Pat. No. 4,565,740.

Stents are made of a biocompatible material such as, e.g. stainless steel, tantalum, titanium, nitinol, gold, platinum, inconel, iridium, silver, tungsten, or another biocompatible metal, or alloys of any of these. Stainless steel and tantalum are particularly useful. Said stent can be covered by one or more layers of a biocompabible coating material such as, e.g. carbon, carbon fiber, cellulose acetate, cellulose nitrate, silicone, parylene, parylene derivatives, polyethylene teraphthalate, polyurethane, polyamide, polyester, polyorthoester, polyanhydride, polyether sulfone, polycarbonate, polypropylene, high molecular weight polyethylene, polytetrafluoroethylene, or another bicompatible material, or mixture or copolymers of these. Parylene is both a generic name for a known group of polymers based on p-xylene and made by vapor phase polymerization, and a name for the unsubstituted one of such polymers. Said one or more layers of biocompatible material comprise a compound of formula (I) of the present invention and advantageously provide a controlled release of said compound of formula (I) effective in preventing, treating or reducing smooth muscle cell proliferation. Said one or more layers of biocompatible material can further comprise bioactive materials such as, e.g. heparin or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate nitric oxide, a nitric oxide promoter or another vasodilator; an antimicrobial agent or antibiotic; aspirin, ticlopdine, a glycoprotein IIb/IIIa inhibitor or another inhibitor of surface glycoprotein receptors, or another antiplatelet agent; colchicine or another antimitotic, or another microtubule inhibitor; a retinoid or another antisecretory agent; cytochalasin or another actin inhibitor; deoxyribonucleic acid, an antisense nucleotide or another agent for molecular genetic intervention; methotrexate or another antimetabolite or antiproliferative agent; an anticancer chemotherapeutic agent; dexamethasone, dexamethasone sodium phosphate, dexamethasone acetate or another dexamethasone derivative, or another anti-inflammatory steroid or non-steroidal antiinflammatory agent; cyclosporin or another immunosuppressive agent; trapidal (a PDGF antagonist), angiopeptin (a growth hormone antagonist), an anti-growth factor antibody, or another growth factor antagonist; dopamine, bromocriptine mesylate, pergolide mesylate or another dopamine agonist: captopril, enalapril or another angiotensin converting enzyme (ACE) inhibitor; ascorbic acid, alphatocopherol, superoxide dismutase, deferoxamine, a 21-aminosteroid (lasaroid) or another free radical scavenger; or a mixture of any of these.

Hence, the present invention further provides a method of treating vascular proliferative disorders in a warm-blooded animal, such as percutaneous transluminal coronary angioplasty restenosis or coronary artery stent restenosis, which comprises administering to said warm-blooded animal a prophylactically or therapeutically effective amount of a compound of formula (I).

In particular said warm-blooded animal is a mammal or more specifically a human.

As is known to those skilled in the art, a prophylactically or therapeutically effective amount varies with the type of therapeutic agent. It is known to those skilled in the art how to determine a prophylactically or therapeutically effective amount of a suitable therapeutic agent.

In view of their useful pharmacological properties, the subject compounds may be formulated into various pharmaceutical forms for administration purposes. To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.0001 mg/kg to 100 mg/kg body weight, and in particular from 0.001 mg/kg to 10 mg/kg body weight. It may be appreciated to administer the required dose as two, three, four or more sub-doses at appropriate intervals throughout the day. Said sub-doses may be formulated as unit dosage forms, for example, containing 0.01 to 500 mg, and in particular 0.1 mg to 200 mg of active ingredient per unit dosage form.

Experimental part

Hereinafter "THF" means tetrahydrofuran, "DIPE" means diisopropylether, "DCM" means dichloromethane, "DMF" means N,N-dimethylformamide and "ACN" means acetonitrile. Of some compounds of formula (I) the absolute stereochemical configuration was not experimentally determined. In those cases the stereochemically isomeric form which was first isolated is designated as "A" and the second as "B", without further reference to the actual stereochemical configuration.

A. Preparation of the intermediates

EXAMPLE A.1

1a) N-Phenyl-3-(3-chlorophenyl)-2-propenamide (58.6 g) and polyphosphoric acid (580 g) were stirred at 100° C. overnight. The product was used without further purification, yielding quant. (±)-4-(3-chlorophenyl)-3,4-dihydro-2(1H)-quinolinone (interm. 1-a).

1b) Intermediate (1-a) (58.6 g), 4-chlorobenzoic acid (71.2 g) and polyphosphoric acid (580 g) were stirred at 140° C. for 48 hours. The mixture was poured into ice water and filtered off. The precipitate was washed with water, then with a diluted $NH_4OH$ solution and taken up in DCM. The organic layer was dried, filtered off and evaporated. The residue was purified by column chromatography over silica gel (eluent:$CH_2Cl_2$/$CH_3OH$/$NH_4OH$ 99/1/0.1). The pure fractions were collected and evaporated, and recrystallized from $CH_2Cl_2$/$CH_3OH$/DIPE, yielding (2.2 g of (±)-6-(4-chlorobenzoyl)-4-(3-chlorophenyl)-3,4-dihydro-2(1H)-quinolinone (interm. 1-b, mp. 194.8° C.).

1c) Bromine (3.4 ml) in bromobenzene (80 ml) was added dropwise at room temperature to a solution of intermediate (1-b) (26 g) in bromobenzene (250 ml) and the mixture was stirred at 160° C. overnight. The mixture was cooled to room temperature and basified with $NH_4OH$. The mixture was evaporated, the residue was taken up in ACN and filtered off. The precipitate was washed with water and air dried, yielding 24 g (92.7%) of product. A sample was recrystallized from $CH_2Cl_2$/$CH_3OH$/DIPE, yielding 2.8 g of 6-(4-chlorobenzoyl)-4-(3-chlorophenyl)-2(1H)-quinolinone; mp. 234.8° C. (interm. 1-c).

1d) Iodomethane (6.2 ml) was added to a mixture of intermediate (1-c) (20 g) and benzyltriethylammonium chloride (5.7 g) in tetrahydrofuran (200 ml) and sodium hydroxide (10N) 200 ml) and the mixture was stirred at room temperature overnight. ethyl acetate was added and the mixture was decanted. The organic layer was washed with water, dried, filtered off and evaporated till dryness. The residue was purified by column chromatography over silica gel (eluent: $CH_2Cl_2$/$CH_3OH$/$NH_4OH$ 99.75/0.25/0.1). The pure fractions were collected and evaporated, yielding 12.3 g (75%) of 6-(4-chlorobenzoyl)-4-(3-chlorophenyl)-1-methyl-2(1H)-quinolinone; mp. 154.7° C. (interm. 1-d).

In a similar way, but starting from intermediate (1-b), (±)-6-(4-chlorobenzoyl)-4-(3-chlorophenyl)-3,4-dihydro-1-methyl-2(1H)-quinolinone (interm 1-e) was prepared.

EXAMPLE A.2

Butyllithium in hexane (1.6 M) (12.75 ml) was added dropwise at −20° C. under $N_2$ to a solution of 6-bromo-4-(3-chlorophenyl)-2-methoxyquinoline (6.7 g) in THF (60 ml) and the mixture was stirred at −20° C. for 30 minutes. A solution of (1-butyl-1H-imidazol-5-yl)(4-chlorophenyl) methanone (3.35 g) in tetrahydrofuran (30 ml) was added at −20° C. under $N_2$ and the mixture was stirred at room temperature for one night. Water was added and the mixture was extracted with ethyl acetate. The organic layer was dried, filtered off and evaporated. The residue was purified by column chromatography over silica gel (eluent: $CH_2Cl_2$/$CH_3$/OH/$NH_4OH$ 97/3/0.1). The pure fractions were collected and evaporated, yielding 2.5 g (total 48%) of (±)-α-(1-butyl-1H-imidazol-5-yl)-4-(3-chlorophenyl)-a-(4-chlorophenyl)-2-methoxy-6-quinoline-methanol (interm. 2).

EXAMPLE A.3

3a) Butyllithium (30.1 ml) was added slowly at −78° C. to a solution of N,N-dimethyl-1H-imidazol-1-sulfonamide (8.4 g) in tetrahydrofuran (150 ml) and the mixture was stirred at −78° C. for 15 minutes. Chlorotriethylsilane (8.1 ml) was added and the mixture was stirred till the temperature reached 20° C. The mixture was cooled till −78° C., butyllithium (30.1 ml) was added, the mixture was stirred at −78° C. for 1 hour and allowed to reach −15° C. The mixture was cooled again till −78° C., a solution of 6-(4-chlorobenzoyl)-1-methyl-4-phenyl-2(1H)-quinolinone (15 g) in tetrahydrofuran (30 ml) was added and the mixture was stirred till the temperature reached 20° C. The mixture was hydrolized and extracted with ethyl acetate. The organic layer was dried, filtered off and evaporated till dryness. The product was used without further purification, yielding 26 g (100%) of (±)-4-[(4-chlorophenyl)(1,2-dihydro-1-methyl-2-oxo-4-phenyl-6-quinolinyl)hydroxymethyl]-N,N-dimethyl-2-(triethylsilyl)-1H-imidazole-1-sulfonamide (interm. 3-a).

A mixture of intermediate (3-a) (26 g) in sulfuric acid (2.5 ml) and water (250 ml) was stirred and heated at 110° C. for 2 hours. The mixture was poured into ice, basified with NH$_4$OH and extracted with DCM. The organic layer was dried, filtered off and evaporated till dryness. The residue was purified by column chromatography over silica gel (eluent: CH$_2$Cl$_2$/CH$_3$OH/NH$_4$OH 99/1/0.2). The pure fractions were collected and evaporated, yielding 2.4 g (11%) of (±)-4-[(4-chlorophenyl)(1,2-dihydro-1-methyl-2-oxo-4-phenyl-6-quinolinyl)hydroxymethyl]-N,N-dimethyl-1H-imidazole-1-sulfonamide (interm. 3-b).

EXAMPLE A.4

Compound (3) (3 g) was added at room temperature to thionyl chloride (25 ml). The mixture was stirred and refluxed at 40° C. overnight. The solvent was evaporated till dryness. The product was used without further purification, yielding 3.49 g of (±)-4-(3-chlorophenyl-1-methyl-6-[1-(4-methylphenyl)-1-(4-methyl-4H-pyrrol-3-yl)ethyl]-2(1H)-quinolinone hydrochloride (interm. 4).

EXAMPLE A.5 a) Toluene (1900 ml) was stirred in a round bottom flask (5 l) using a water separator (4-Chlorophenyl)(4-nitrophenyl)methanone (250 g) was added portionwise. p-Toluene-sulfonic acid (54.5 g) was added portionwise. Ethylene glycol (237.5 g) was poured out into the mixture. The mixture was stirred and refluxed for 48 hours. The solvent was evaporated. The residue was dissolved into ethyl acetate (5 l) and washed twice with a K$_2$CO$_3$ 10% solution. The organic layer was separated, dried, filtered and the solvent was evaporated. The residue was stirred in DIPE, filtered off and dried (vacuum, 40° C., 24 hours), yielding 265 g (91%) of 2-(4-chlorophenyl)-2-(4-nitrophenyl)-1,3-dioxolane (interm. 5-a).

b) Sodium hydroxide (16.4 g) and (3 methoxyphenyl) acetonitrile (20.6 ml) were added at room temperature to a solution of interm. (5-a) (25 g) in methanol (100 ml) and the mixture was stirred at room temperature overnight. Water was added, the precipitate was filtered off, washed with cold methanol and dried. The product was used without further purification, yielding 30 g (90%) of 5-[2-(4-chlorophenyl)-1,3-dioxolan-2-yl]-3-(3-methoxyphenyl)-2,1-benzisoxazole (interm. 5-b).

c) Interm. (5-b) (30 g) in THF (250 ml) was hydrogenated with palladium on carbon (3 g) as a catalyst at room temperature for 12 hours under a 2.6 10$^5$ Pa pressure in a Parr apparatus. After uptake of H$_2$(1 equivalent), the catalyst was filtered through celite and the filtrate was evaporated till dryness. The product was used without further purification, yielding 31.2 g (100%) of (3-methoxyphenyl)[2-amino-5-[2-(4-chlorophenyl)-1,3-dioxolan-2-yl]phenyl]methanone (interm. 5-c).

d) Acetic anhydride (13.9 ml) was added to a solution of interm. (5-c) (31.2 g) in toluene (300 ml) and the mixture was stirred and refluxed for 2 hours. The mixture was evaporated till dryness and the product was used without further purification, yielding 36.4 g (100%) of N-[2-(3-methoxybenzoyl)-4-[2-(4-chlorophenyl)-1,3-dioxolan-2-yl]phenyl]acetamide (interm. 5-d).

e) Potassium tert-butoxide (33 g) was added portionwise at room temperature to a solution of interm. (5-d) (36.4 g) in 1.2-dimethoxyethane (350 ml) and the mixture was stirred at room temperature overnight. The mixture was hydrolized and extracted with DCM. The organic layer was dried, filtered off and evaporated till dryness. The product was used without further purification, yielding 43 g of 6-[2-(4-chlorophenyl)-1,3-dioxolan-2-yl]-4-(3-methoxyphenyl)-2(1H)-quinolinone (interm. 5-e).

f) A mixture of interm. (5-e) (43 g) in HCl (3N, 400 ml) and methanol (150 ml) was stirred and refluxed overnight. The mixture was cooled and filtered off. The precipitate was washed with water and diethyl ether and dried. The product was used without further purification, yielding 27 g (94%) of 6-(4-chlorobenzoyl)-4-(3-methoxyphenyl)-2(1H)-quinolinone (interm. 5-f).

g) Methyl iodide (1.58 ml) was added to a solution of interm. (5-f) (7.6 g) and benzyl-triethylammonium chloride (BTEAC) (2.23 g) in THF (80 ml) and sodium hydroxide (40%, 80 ml). The mixture was stirred at room temperature for 2 hours. Water was added and the mixture was extracted with ethyl acetate. The organic layer was dried, filtered, and the solvent was evaporated. The residue was purified by flash column chromatography over silica gel (eluent: DCM 100%). The desired fractions were collected and the solvent was evaporated, yielding 7.1 g (90%) of 6-(4-chlorobenzoyl)-4-(3-methoxyphenyl)-1-methyl-2(1H)-quinolinone (interm. 5-g).

EXAMPLE A.6 a) 3-(3-Chlorophenyl)-5-[2-(4-chlorophenyl)-1,3-dioxolan-2-yl]-2,1-benzisoxazole (interm. 6-a) was prepared analogous as intermediate (5-b).

b) A mixture of intermediate (6-a) (30 g) in HCl 3 N (220 ml) and methanol (165 ml) was stirred at 100° C. for 5 hours. The mixture was poured into ice and basified with NH$_3$ (aq.). The precipitate was filtered off, washed with water and diethyl ether and dried, yielding 24.9 g (93%) of (4-chlorophenyl)[3-(3-chlorophenyl)-2,1-benzisoxazol-5-yl]methanone (interm. 6-b). The product was used without further purification.

c) Butyllithium in hexanes (10 ml) was added slowly at −70° C. under $N_2$ flow to a solution of 1-methylimidazole (1.31 g) in THF (30 ml). The mixture was stirred at −70° C. for 45 minutes. Chlorotriethylsilane (2.7 ml) was added. The mixture was allowed to warm to 15° C. and cooled to −70° C. Butyllithium (10 ml) was added slowly. The mixture was stirred at −70° C. for 1 hour, allowed to warm to −15° C. and cooled to −70° C. A solution of intermediate (6-b) (4.9 g) in THF (60 ml) was added. The mixture was stirred at −70° C. for 30 minutes, then hydrolyzed with water, extracted with ethyl acetate and decanted. The organic layer was dried, filtered and the solvent was evaporated. The residue (8.2 g) was purified by column chromatography over silica gel (eluent: $CH_2Cl_2/CH_3OH/NH_4OH$ 96/4/0.2) and crystallized from 2-propanone/diethyl ether. The precipitate was filtered off and dried, yielding 1.5 g (25%) of (±)-3-(3-chlorophenyl)-α-(4-chlorophenyl-α-(1-methyl-1H-imidazol-5-yl)-2,1-benzisoxazole-5-methanol (interm. 6-c).

d) $TiCl_3$/15% in $H_2O$ (200 ml) was added at room temperature to a solution of intermediate (6-c) (38 g) in THF (300 ml). The mixture was stirred at room temperature for 90 minutes. The mixture was poured out on ice, basified with $K_2CO_3$, filtered over celite, washed with ethyl acetate and decanted. The organic layer was dried, filtered and the solvent was evaporated. The residue was purified by column chromatography over silica gel (eluent: $CH_2Cl_2/CH_3OH/NH_4OH$ 97/3/0.1 and 95/5/0.1), yielding 18.7 g (49%) of (±)-[2-amino-5-[4-chlorophenyl)hydroxy(1-methyl-1H-imidazol-5-yl)methyl]phenyl](3-chlorophenyl)methanone (interm. 6-d).

B. Preparation of the final compounds

EXAMPLE B.1

1-Methylimidazole (4.69 ml) in tetrahydrofuran (100 ml) was stirred at −78° C. A solution of butyllithium in hexanes (2.5 M) (36.7 ml) was added dropwise and the mixture was stirred at −78° C. for 15 minutes. Chlorothiethylsilane (9.87 ml) was added and the mixture was brought to room temperature. The mixture was cooled till −78° C., a solution of butyllithium in hexane (2.5 M) (36.7 ml) was added dropwise, the mixture was stirred at −78° C. for 1 hour and brought till −15° C. The mixture was cooled till −78° C. a solution of intermediate (1-d) (20 g) in THF (40 ml) was added and the mixture was brought to room temperature. The mixture was hydrolized at 0° C. and extracted with ethyl acetate. The organic layer was dried, filtered off and evaporated till dryness, yielding 36 g of product. The product was purified by column chromatography over silica gel (eluent: $CH_2Cl_2/CH_3OH/NH_4OH$ 97/3/0.1). The pure fractions were collected, evaporated, and crystallized from 2-propanone, $CH_3OH$ and $(C_2H_5)_2O$. The precipitate was filtered off, washed with $(C_2H_5)_2O$ and dried, yielding 12.4 g (52%) of (±)-4-(3-chlorophenyl)-6-[(4-chlorophenyl)hydroxyl(1-methyl-1H-imidazol-5-yl)methyl]-1-methyl-2(1H)-quinolinone; (comp. 3, mp.233.6° C.). In a similar way, but using intermediate (5-g) or intermediate (1e) instead of intermediate (1-d), respectively (±)-6-[(4-chlorophenyl) hydroxy(1-methyl-1H-imidazol-5-yl)methyl]-4-(3-methoxyphenyl)-1-methyl-2(1H)-quinolinone (comp. 36) and (±)-4-(3-chlorophenyl)-6-[(4-chlorophenyl)hydroxy(1-methyl-1H-imidazol-5-yl)methyl]-3,4-dihydro-1-methyl-2 (1H)-quinolinone (comp. 127) were prepared.

EXAMPLE B.2

Hydrochloric acid (60 ml) was added to a solution of intermediate (2) (2.5 g) in THF (10 ml) and the mixture was stirred and heated at 100° C. for 3 hours. The mixture was cooled, the precipitate was filtered off, washed with water, then with diethyl ether and dried, yielding 2.7 g (100%) of (±)-6-[(1-butyl-1H-imidazol-5-yl)-(4-chlorophenyl) hydroxymethyl]-4-(3-chlorophenyl)-2(1H)-quinolinone (comp. 8).

EXAMPLE B.3

Sodium hydride (0.28 g) was added to a mixture of compound (3) (3 g) in DMF (50 ml) under $N_2$ and the mixture was stirred for 15 minutes. Iodomethane (1.5 ml) was added and the mixture was stirred at room temperature for 1 hour. The mixture was hydrolized and extracted with diethyl ether and methanol. The organic layer was dried, filtered off and evaporated till dryness, yielding 4.4 g of residue. The residue was purified by column chromatography over silica gel (eluent: $CH_2Cl_2/CH_3OH/NH_4OH$ 95.5/4.5/0.2). The pure fractions were collected and evaporated. The product was converted into the ethanedioic acid salt (1:1) in 2-propanone and filtered off. The residue was crystallized from 2-propanone, diethyl ether and DIPE. The precipitate was filtered off, washed with diethyl ether, dried and recrystallized from 2-propanone, methanol and DIPE. The precipitate was filtered off, washed with diethyl ether and dried, yielding 0.95 g (25%) of (±)-4-(3-chlorophenyl)-6-[(4-chlorophenyl)methoxy(1-methyl-1H-imidazol-5-yl) methyl]-1-methyl-2(1H)-quinolinone ethanedioate(1:1) .dihydrate; (comp. 4, mp. 154.6° C.).

EXAMPLE B.4

Iodomethane (0.38 ml) was added dropwise at room temperature to a solution of compound (8) (2.44 g) and N,N,N-triethylbenzenemethanaminium chloride (0.54 g) in tetrahydrofuran (30 ml) and sodium hydroxide (40%) (30 ml) and the mixture was stirred at room temperature for 3 hours. Water was added and the mixture was extracted with ethyl acetate. The organic layer was dried, filtered off and evaporated. The residue was purified by column chromatography over silica gel (eluent: $CH_2Cl_2/CH_3OH/NH_4OH$ 96.5/3.5/0.1). The pure fractions were collected, evaporated and crystallized from 2-propanone and DIPE. The precipitate was filtered off, washed with diethyl ether and dried, yielding 1.4 g (56%) of (±)-4-(3-chlorophenyl)-6-[(1-butyl-1H-imidazol-5-yl)(4-chlorophenyl)hydroxymethyl]-1-methyl-2(1H)-quinolinone; (comp. 9, mp. 174.6° C).

EXAMPLE B.5

Iodomethane (1.4 ml) was added to a mixture of (±)-6-[(4-chlorophenyl)-1H-imidazol-4-ylmethyl]-1-methyl-4-phenyl-2(1H)-quinolinone (7.5 g) and benzyltriethylammonium chloride (2 g) in THF (75 ml) and sodium hydroxide (75 ml) and the mixture was stirred at room temperature for 1 hour. Water was added and the mixture was extracted with ethyl acetate. The organic layer was dried, filtered off and evaporated till dryness. The residue was purified by column chromatography over silica gel (eluent: $CH_2Cl_2/CH_3OH/NH_4OH$ 98.5/1.5/0.2). The pure fractions were collected and evaporated. Fraction 1 (3.5 g) was recrystallized from diethyl ether, yielding 3.3 g (42%) of (=-6-[(4-chlorophenyl) (1-methyl-1H-imidazol-4-yl)methyl]-1-methyl-4-phenyl-2 (1H)-quinolinone: mp. 149.9° C. (comp. 44). Fraction 2 was recrystallized from 2-propanone, methanol and diethyl ether, yielding 1.6 g (20%) of (±)-6-[(4-chlorophenyl)(1-methyl-1H-imidazol-5-yl)methyl]-1-methyl-4-phenyl-2(1H)-quinolinone (comp. 2, mp. 96.8° C.).

EXAMPLE B.6

Sodium borohydride (5.6 g) was added portionwise at 0° C. under $N_2$ to compound (3) (7.2 g) dissolved in trifluoroacetic acid (150 ml) and the mixture was stirred at room temperature overnight. The mixture was poured into ice, basified with NaOH 3N, then concentrated NaOH and extracted with ethyl acetate. The organic layer was dried, filtered off and evaporated till dryness. The residue was purified by column chromatography over silica gel (eluent: $CH_2Cl_2/CH_3OH$ 95/5). The pure fractions were collected and evaporated, yielding 4.3 g (62%) of fraction 1; 0.2 g (3%) of fraction 2 and 2 g (29%) of fraction 3. Fraction 1 was converted into the ethanedioic acid salt (1:1) in 2-propanone and diethyl ether. The precipitate was filtered off, washed with diethyl ether and dried, yielding 4.7 g (55%) of (±)-4-(3-chlorophenyl)-6-[(4-chlorophenyl)(1-methyl-1H-imidazol-5-yl)methyl]-1-methyl-2(1H)-quinolinone ethanedioate(1:1).mono-hydrate (comp. 5, mp. 157.4° C.).

EXAMPLE B.7

A solution of compound 90 (4.2 g) in 1,2-dimethoxyethane (70 ml) was stirred under $N_2$ for 30 minutes. Iodomethane (0.83 ml), followed by potassium tert-butoxide (2 g) were added portionwise and the mixture was stirred at room temperature for 30 minutes. Water was added and the mixture was extracted with ethyl acetate. The organic layer was dried, filtered off and evaporated. The residue was purified by column chromatography over silica gel (eluent: cyclohexane/2-propanol/$NH_4OH$ 85/5/0.5 to 80/20/1) and converted into the ethanedioic acid salt, crystallized from 2-propanone and filtered off, yielding 1.16 g (23.6%) of (±)-4-(3-chlorophenyl)-6-[1-(4-chloro-phenyl)-1-(1-methyl-1H-imidazol-5-yl)ethyl]-1-methyl-2(1H)-quinolinone.ethanedioate (1:1); (comp. 12, mp. 203.9° C.). In a similar way, but replacing iodomethane by dichloromethane or dibromomethane, respectively (±)-6-[2-chloro-1-(4-chlorophenyl)-1-(1-methyl-1H-imidazol-5-yl) ethyl]-4-(3-chlorophenyl)-1-methyl-2(1H)-quinolinone ethanedioate (1:1) (comp. 69) and (±)-6-[2-bromo-1-(4-chlorophenyl)-1-(1-methyl-1H-imidazol-5-yl)ethyl]-4-(3-chlorophenyl)-1-methyl-2(1H)-quinolinone (comp. 70) were prepared.

EXAMPLE B.8 a) Compound (3) (3 g) was separated (into its enantiomers) and purified by high-performance liquid chromatography over Chiracel OD (20 μm; eluent:hexane/ethanol (50/50). The pure (A)-fractions were collected, and the solvent was evaporated, yielding 1.6 g ((A); LCI: >99%). The pure (B)-fractions were collected, and the solvent was evaporated, yielding 1.5 g ((B); LCI: >99%). The (A)-residue was dissolved in 2-propanol and converted into the ethanedioic acid salt (1:1). The precipitate was filtered off and dried, yielding 0.6 g (17%) of (±)-4-(3-chlorophenyl)-6-[(4-chloro-phenyl)-hydroxy(1-methyl-1H-imidazol-5-yl) methyl]-1-methyl-2(1H)-quinolinone ethanedioate (1:1); $[\alpha]_{20}^D$=+17.96° (c=1% in methanol) (comp. 23). The (B)-residue was dissolved in 2-propanol and converted into the ethanedioic acid salt (1:1). The precipitate was filtered off and dried, yielding 0.6 g (17%) (−)-4-(3- chlorophenyl)-6-[(4-chlorophenyl)hydroxy(1-methyl-1H-imidazol-5-yl) methyl]-1-methyl-2(1H)-quinolinone ethanedioate(1:1); $[\alpha]_D^{20}$=−18.87° (c=1% (w/v) in methanol) (comp. 24).

b) Compound 14 (4 g) was separated (into its enantiomers) and purified by chiral column chromatography over Chiralcel OD (25 cm; eluent: 100% ethanol; flow: 0.5 ml/min; wavelength: 220 nm). The pure (A)-fractions were collected, and the solvent was evaporated. This residue was dissolved in DCM (100 ml), filtered, and the filtrate was evaporated. The residue was stirred in DIPE (100 ml), filtered off and dried, yielding 1.3 g (−)-6-[amino(4-chlorophenyl)(1-methyl-1H-imidazol-5-yl)methyl]-4-(3-chloro-phenyl)-1-methyl-2(1H)-quinolinone ($[\alpha]_D^{20}$=−6.16° (c=0.67% (w/v) in methanol) (comp. 74).

The pure (B)-fractions were collected and evaporated. The residue was crystallized from 2-propanol. The precipitate was filtered off, yielding 1.3 g (+)-6-[amino(4-chlorophenyl)(1-methyl-1H-imidazol-5-yl)methyl]-4-(3-chlorophenyl)-1-methyl-2(1H)-quinolinone ($[\alpha]_D^{20}$=+22.86° (c=0.98% (w/v) in methanol) (comp. 75).

EXAMPLE B.9

Air was bubbled through a solution of compound (47) (3.6 g) in THF (40 ml) for 30 minutes. 2-Methyl-2-propanol potassium salt (4.4 g) was added. The mixture was stirred at room temperature for 3 hours, hydrolyzed and then extracted with DCM. The organic layer was separated, dried, filtered and the solvent was evaparated, yielding 2.9 g of product. The product was purified by column chromatography over silica gel (eluent: $CH_2Cl_2/CH_3OH/NH_4OH$ 97.5/2.5/0.1). The pure fractions were collected and the solvent was evaporated. The residue was crystallized from 2-propanone/DIPE. The precipitate was filtered off and dried, yielding 1.3 g (35%) of (±)-4-(3-chlorophenyl)-6-[(4-chlorophenyl) hydroxy(1-methyl-1H-imidazol-4-yl)methyl]-1-methyl-2 (1H)-quinolinone (comp. 48).

EXAMPLE B.10

A mixture of (±)-4-[(4-chlorophenyl)(1,2-dihydro-1-methyl-2-oxo-4-phenyl-6-quinolinyl)hydroxymethyl]-N,N-dimethyl-1H-imidazole-1-sulfonamide (2.4 g) in hydrochloric acid (10 ml), water (30 ml) and methanol (15 ml) was stirred and heated at 110° C. for 14 hours. The mixture was cooled, basified with $NH_3$ (aq.) and extracted with DCM. The organic layer was dried, filtered off and evaporated till dryness. The residue was purified by column chromatography over silica gel (eluent: $CH_2Cl_2/CH_3OH/NH_4OH$ 95/5/

0.2). The pure fractions were collected and evaporated. The residue (1.25 g) was crystallized from 2-propanone/DIPE, yielding 1 g (48.3%) of (±)-6-[(4-chlorophenyl)hydroxy (1H-imidazol-4-yl)methyl]-1-methyl-4-phenyl-2(1H)-quinolinone monohydrate (comp. 43).

EXAMPLE B.11

Compound (3) (4 g) was dissolved in DCM (10 ml) and acetic acid (5.6 ml) at 45° C. Zinc chloride (5.5 g), followed by cyanoacetic acid (3.5 g) were added. The mixture was stirred at 120° C. for 3 hours and then at 160° C. for 10 hours. Water was added and the mixture was extracted with DCM. The organic layer was washed with $K_2CO_3$ 10%, dried, filtered, and the solvent was evaporated. The residue was purified by column chromatography over silica gel (eluent: $CH_2Cl_2/CH_3OH/NH_4OH$ 96/4/0.2), crystallized from 2-propanone/DIPE, filtered off and dried, yielding 1.95 g (45%) of (±)-4-(3-chlorophenyl)-β-(4-chlorophenyl)-1,2-dihydro-1-methyl-β-(1-methyl-1H-imidazol-5-yl)-2-oxo-6-quinolinepropanenitrile; (comp. 25, mp. 151.3° C.).

EXAMPLE B.12

Sulfuric acid (1 ml) was added dropwise to acetonitrile (30 ml), while stirring. Compound 3 (3 g) was added. The mixture was stirred at 80° C. for 3 hours and then cooled. $K_2CO_3$ 10% was added and the mixture was extracted with ethyl acetate. The organic layer was separated, dried, filtered and the solvent was evaporated till dryness. The residue (3.58 g) was dissolved in 2-propanone and converted into the ethanedioic acid salt (1:1). The precipitate was filtered off, dried and crystallized from 2-propanone/$CH_3OH$. The precipitate was filtered off and dried, yielding 3.5 g (92%) of (±)-N-[(4-chlorophenyl)[4-(3-chlorophenyl)-1,2-dihydro-1-methyl-2-oxo-6-quinolinyl](1-methyl-1H-imidazol-5-yl)methyl]acetamide ethanedioate (1:1) (comp. 56).

EXAMPLE B.13

$NH_3$ (aq.) (40 ml) was added at room temperature to a mixture of intermediate 4 (7 g) in THF (40 ml). The mixture was stirred at 80° C. for 1 hour, then hydrolyzed and extracted with DCM. The organic layer was separated, dried, filtered and the solvent was evaporated. The residue was purified by column chromatography over silica gel (eluent: toluene/2-propanol/$NH_4OH$ 80/20/1). The pure fractions were collected and the solvent was evaporated, yielding 4.4 g (±)-6-[amino(4-chlorophenyl)(1-methyl-1H-imidazol-5-yl)methyl]-4-(3-chlorophenyl)-1-methyl-2(1H)-quinolinone (comp. 14).

EXAMPLE B.14

A solution of compound 36 (6.2 g) in DCM (140 ml) was cooled and tribromoborane (32 ml) was added dropwise. The mixture was stirred at room temperature for tho days. The mixture was poured out into ice water, basified with $NH_3$ (aq.) and extracted with $CH_2Cl_2/CH_3OH$. The organic layer was separated, dried, filtered and the solvent was evaporated till dryness, yielding 6 g (100%) of (±)-6-[(4-chlorophenyl)-hydroxy-(1-methyl-1H-imidazol-5-yl)methyl]-4-(3-hydroxyphenyl)-1-methyl-2(1H)-quinolinone (comp. 54).

EXAMPLE B.15

A mixture of compound 54 (2.5 g), 2-chloro-N,N-dimethyl-ethanamine (1.9 g) and potassium carbonate (2.2 g) in ACN (50 ml) and DMF (50 ml) was stirred at 100° C. overnight. The solvent was evaporated till dryness. The residue was taken up in $CH_2Cl_2$/water and decanted. The organic layer was dried, filtered and the solvent was evaporated. The residue (2.7 g) was purified by column chromatography over silica gel (eluent: $CH_2Cl_2/CH_3OH/NH_4OH$ 97/3/0.1 to 90/10/0.1). The pure fractions were collected and the solvent was evaporated. The residue was converted into the ethanedioic acid salt (1:1) in 2-propanone. The precipitate was filtered off, washed with 2-propanone/diethyl ether and dried. The residue was converted into the free base. The precipitate was filtered off and dried. The residue was crystallized from diethyl ether. The precipitate was filtered off and dried, yielding 0.35 g (12%) of (±)-6-[(4-chlorophenyl)hydroxy(1-methyl-1H-imidazol-5-yl)methyl]-4-[3-[2-(dimethylamino)ethoxy]-phenyl]-1-methyl-2(1H)-quinolinone (comp. 62).

EXAMPLE B.16

$P_4S_{10}$ (12 g) was added to a mixture of compound 90 (6 g) in pyridine (72 ml). The mixture was stirred and refluxed for 6 hours. Ice water was added. The precipitate was filtered off, washed with water and taken up in DCM. The organic layer was separated, dried, filtered and the solvent was evaporated till dryness. The residue was purified by column chromatography over silica gel (eluent: $CH_2Cl_2/CH_3OH/NH_4OH$ 97.5/2.5/0.1). The pure fractions were collected and the solvent was evaporated. The residue was crystallized from 2-propanone/diethyl ether. The precipitate was filtered off and dried, yielding 1 g of (±)-4-(3-chlorophenyl)-6-[(4-chlorophenyl)(1-methyl-1H-imidazol-5-yl)methyl]-1-methyl-2(1H)-quinolinethione (comp. 128).

EXAMPLE B.17

A mixture of ethyl malonyl chloride (6.4 ml) in DCM (50 ml) was added dropwise at room temperature to a solution of intermediate (6-d) (15 g) and pyridine (10.7 ml) in DCM (150 ml). The mixture was stirred at room temperature overnight. Water was added and the mixture was decanted. The organic layer was dried, filtered and the solvent was evaporated. The residue (21 g) was purified by column chromatography over silica gel (eluent: $CH_2Cl_2$/2-propanol/$NH_4OH$ 92/8/0.4). The desired fractions were collected and the solvent was evaporated, yielding 10.9 g (60%) of (±)-ethyl 4-(3-chlorophenyl)-6-[(4-chlorophenyl)hydroxy(1-methyl-1H-imidazol-5-yl)methyl]-1,2-dihydro-2-oxo-3-quinolinecarboxylate (comp. 144).

EXAMPLE B.18 a) A mixture of benzoyl chloride (3.1 ml) in DCM (25 ml) was added dropwise at room temperature to a solution of interm. (6-d) (7 g) and pyridine (5 ml) in DCM (70 ml). The mixture was stirred at room temperature for 45 minutes. Water was added and the mixture was decanted. The organic layer was dried, filtered and the solvent was evaporated, yielding 8.8 g of (±)-N-[2-(3-chlorobenzoyl)-4-[(4-chlorophenyl)hydroxy(1-methyl-1H-imidazol-5-yl)methyl]

phenyl]benzeneacetamide (interm. 7). The product was used without further purification.

b) Potassium tert-butoxide (8.7 g) was added to a mixture of intermediate 7 (8.8 g) in DME (70 ml). The mixture was stirred at 50° C. for 3 hours. Water (5 ml) was added and the solvent was evaporated, yielding 8.5 g of (±)-4-(3-chlorophenyl)-6-[(4-chlorophenyl)hydroxy(1-methyl-1H-imidazol-5-yl)methyl]-3-phenyl-2(1H)-quinoline (comp. 140).

EXAMPLE B.19

$NH_3$ (aq.) (150 ml) was cooled to 5° C. A solution of (±)-4-(3-chlorophenyl)-1-methyl-6-[1-(4-methylphenyl)-1-(4-methyl-4H-pyrrol-3-yl)ethyl]-2(1H)-quinolinone hydrochloride (16.68 g) in THF (150 ml) was added. The mixture was stirred at room temperature for 2 hours, decanted and extracted with ethyl acetate. The organic layer was dried, filtered and the solvent was evaporated till dryness. The reaction was carried out twice. The residues were combined and purified by column chromatography over silica gel (eluent: toluene/2-propanol/$NH_4OH$ 70-29-1). The pure fractions were collected and the solvent was evaporated. The residue was crystallized from $CH_2Cl_2/CH_3OH/CH_3CN$. The precipitate was filtered off and the mother layer was evaporated till dryness, purified by column chromatography (eluent: $CH_3OH/NH_4OAc$ (0.5% in $H_2O$) 70/30). Two pure fractions were collected and their solvents were evaporated till dryness. Fraction 2 was recrystallized from $CH_2Cl_2$/diethyl ether. The precipitate was filtered off and dried, yielding 0.8 g of (±)-6-[amino(4-chlorophenyl)(1-methyl-1H-imidazol-5-yl)methyl]-3-chloro-4-(3-chlorophenyl)-1-methyl-2(1H)-quinolinone (comp. 143).

EXAMPLE B.20

Sulfuric acid (1 ml) was added at room temperature to a solution of compound 3 (3.5 g) in methoxyacetonitrile (10 ml) and the mixture was stirred and heated at 80° C. for 3 hours. The mixture was cooled, poured into ice, basified with $NH_3$ (aq.) and filtered off. The precipitate was taken up in DCM. The organic layer was separated, dried, filtered and the solvent was evaporated. The residue was purified by column chromatography over silica gel (eluent: $CH_2Cl_2/CH_3OH/NH_4OH$ 96/4/0.3). The pure fractions were collected and the solvent was evaporated. The residue was converted into the hydrochloric acid salt (1:1) and crystallized from ACN. The precipitate was filtered off and dried, yielding 2.5 g (58%) of (±)-N-[(4-chlorophenyl)[4-(3-chlorophenyl)-1,2-dihydro-1-methyl-2-oxo-6-quinolinyl](1-methyl-1H-imidazol-5-yl)methyl]-2-methoxyacetamide monohydrochloride (comp. 89).

EXAMPLE B.21

A solution of intermediate (4) (3.3 g) in THF (10 ml) was added dropwise at room temperature to a solution of methanamine in water (40 ml). The mixture was stirred at 80° C. for 45 minutes, taken up in water and extracted with DCM. The organic layer was separated, dried, filtered and the solvent was evaporated. The residue was purified by column chromatography over silica gel (eluent: $CH_2Cl_2/CH_3OH/NH_4OH$ 97/3/0.3 and 95/5/0.3). The pure fractions were collected and the solvent was evaporated. The residue was crystallized from diethyl ether. The precipitate was filtered off and dried, yielding 0.89 g (28%) of (±)-4-(3-chlorophenyl)-6-[(4-chloro-phenyl)(methylamino)(1-methyl-1H-imidazol-5-yl)methyl]-1-methyl-2(1H)-quinolinone monohydrate (comp. 61).

Tables 1 to 8 list the compounds that were prepared according to one of the above Examples and table 9 lists both the experimental (column heading "exp.") and theoretical (column heading "theor.") elemental analysis values for carbon, hydrogen and nitrogen of the compounds as prepared in the experimental part hereinabove.

TABLE 1

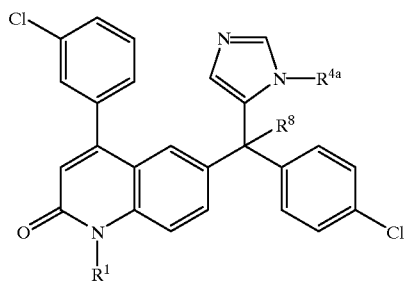

| Co. No. | Ex. No. | $R^1$ | $R^{4a}$ | $R^8$ | Physical data |
|---|---|---|---|---|---|
| 3 | B.1 | $CH_3$ | $CH_3$ | OH | mp. 233.6° C. |
| 4 | B.3 | $CH_3$ | $CH_3$ | $OCH_3$ | mp. 140–160° C.; .$C_2H_2O_4.H_2O$ |
| 5 | B.6 | $CH_3$ | $CH_3$ | H | mp. 165° C.; .$C_2H_2O_4.H_2O$ |
| 6 | B.5 | $CH_3$ | $CH_2CH_3$ | H | mp. 180° C.; .$C_2H_2O_4.½H_2O$ |
| 7 | B.2 | H | $CH_3$ | H | mp. 260° C. |
| 8 | B.2 | H | $(CH_2)_3CH_3$ | OH | — |
| 9 | B.4 | $CH_3$ | $(CH_2)_3CH_3$ | OH | mp. 174° C. |

TABLE 1-continued

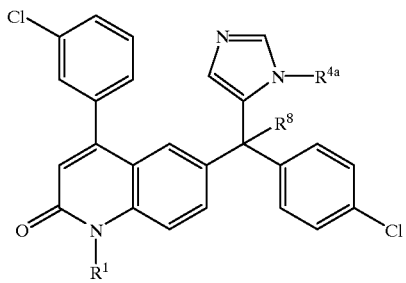

| Co. No. | Ex. No. | $R^1$ | $R^{4a}$ | $R^8$ | Physical data |
|---|---|---|---|---|---|
| 10 | B.3 | H | CH$_3$ | OCH$_2$COOCH$_2$CH$_3$ | mp. 185° C.; .½C$_2$H$_2$O$_4$ |
| 11 | B.3 | CH$_3$ | CH$_3$ | O(CH$_2$)$_2$N(CH$_3$)$_2$ | mp. 120° C. |
| 12 | B.7 | CH$_3$ | CH$_3$ | CH$_3$ | mp. 210° C.; .C$_2$H$_2$O$_4$ |
| 13 | B.7 | CH$_3$ | CH$_3$ | CH$_2$CH$_3$ | mp. 196° C.; .C$_2$H$_2$O$_4$ |
| 14 | B.13 | CH$_3$ | CH$_3$ | NH$_2$ | mp. 220° C. |
| 72 | B.13 | CH$_3$ | CH$_3$ | NH$_2$ | .½-(E)-C$_4$H$_4$O$_4$ |
| 73 | B.13 | CH$_3$ | CH$_3$ | NH$_2$ | .2HCl |
| 74 | B.8b | CH$_3$ | CH$_3$ | NH$_2$ | (−)- |
| 75 | B.8b | CH$_3$ | CH$_3$ | NH$_2$ | (+)-: mp. 232.4° C. |
| 15 | B.3 | CH$_3$ | CH$_3$ | O(CH$_2$)$_3$OH | mp. 135° C. |
| 16 | B.3 | CH$_3$ | CH$_3$ | O(CH$_2$)$_2$CH$_3$ | mp. 180° C.; .C$_2$H$_2$O$_4$.½(H$_2$O) |
| 17 | B.3 | CH$_3$ | CH$_3$ | O(CH$_2$)$_2$O—C$_6$H$_5$ | mp. 144° C.; .½(C$_2$H$_2$O$_4$) |
| 18 | B.2 | H | CH(CH$_3$)$_2$ | OH | — |
| 19 | B.4 | CH$_3$ | CH(CH$_3$)$_2$ | OH | mp. 254° C. |
| 20 | B.2 | H | (CH$_2$)$_2$OCH$_3$ | OH | mp. 112° C. |
| 21 | B.4 | CH$_3$ | (CH$_2$)$_2$OCH$_3$ | OH | mp. 192° C. |
| 22 | B.3 | CH$_3$ | CH$_3$ | O(CH$_2$)$_2$OH | mp. 198° C. |
| 23 | B.8a | CH$_3$ | CH$_3$ | OH | mp. 150–200° C.; (+)-; .C$_2$H$_2$O$_4$ |
| 24 | B.8a | CH$_3$ | CH$_3$ | OH | mp. 150–200° C.; (−)-; .C$_2$H$_2$O$_4$ |
| 25 | B.11 | CH$_3$ | CH$_3$ | CH$_2$—CN | mp. 154° C. |
| 27 | B.2 | H | (CH$_2$)$_3$OCH$_3$ | OH | — |
| 28 | B.4 | CH$_3$ | (CH$_2$)$_3$OCH$_3$ | OH | mp. 196° C.; .H$_2$O |
| 29 | B.3 | CH$_3$ | CH$_3$ | O(CH$_2$)$_3$OCH$_2$CH$_3$ | mp. 105° C.; .½(H$_2$O) |
| 31 | B.2 | H | CH$_3$ | OH | >260° C. |
| 32 | B.6 | CH$_3$ | (CH$_2$)$_2$OCH$_3$ | H | mp. 140° C.; .½(C$_2$H$_2$O$_4$) |
| 33 | B.6 | CH$_3$ | (CH$_2$)$_3$OCH$_3$ | H | mp. 180° C.; .HCl |
| 56 | B.12 | CH$_3$ | CH$_3$ | —NHCOCH$_3$ | .C$_2$H$_2$O$_4$ |
| 58 | B.11 | CH$_3$ | CH$_3$ | —CH$_2$COOCH$_2$CH$_3$ | .C$_2$H$_2$O$_4$.½(H$_2$O) |
| 60 | B.11 | CH$_3$ | CH$_3$ | 1-imidazolyl | — |
| 61 | B.21 | CH$_3$ | CH$_3$ | —NH—CH$_3$ | mp. 164° C. |
| 65 | B.2 | H | (CH$_2$)$_3$SOCH$_3$ | OH | .H$_2$O |
| 66 | B.13 | CH$_3$ | CH$_3$ | —N(CH$_3$)$_2$ | .2C$_2$H$_2$O$_4$.H$_2$O mp. 160° C. |
| 67 | B.13 | CH$_3$ | CH$_3$ | —NH—(CH$_2$)$_2$OCH$_3$ | mp. 216° C. |
| 68 | B.13 | CH$_3$ | CH$_3$ | —NH—(CH$_2$)$_2$—OH | — |
| 69 | B.7 | CH$_3$ | CH$_3$ | —CH$_2$Cl | .2C$_2$H$_2$O$_4$ mp. 220° C. |
| 70 | B.7 | CH$_3$ | CH$_3$ | —CH$_2$Br | — |
| 71 | * | CH$_3$ | CH$_3$ | —CH$_2$OH | .2C$_2$H$_2$O$_4$ |
| 76 | B.4 | —(CH$_2$)$_2$OCH$_3$ | CH$_3$ | OH | mp. 150° C. |
| 77 | * | CH$_3$ | CH$_3$ | —CH$_2$OCH$_3$ | .2C$_2$H$_2$O$_4$ mp. 166° C. |
| 78 | B.13 | CH$_3$ | CH$_3$ | —NH—OCH$_3$ | mp. 170° C. |
| 79 | B.20 | CH$_3$ | CH$_3$ | —NH—CONH$_2$ | .2H$_2$O |
| 80 | ** | CH$_3$ | CH$_3$ | —CH$_2$CONH$_2$ | — |
| 81 | B.13 | CH$_3$ | CH$_3$ | —NH—OH | — |
| 82 | B.13 | CH$_3$ | CH$_3$ | —NH(CH$_2$)$_2$N(CH$_3$)$_2$ | — |
| 83 | B.4 | (CH$_2$)$_2$N(CH$_3$)$_2$ | CH$_3$ | OH | .3/2C$_2$H$_2$O$_4$ .½H$_2$O mp. 200 ° C. |
| 84 | * | CH$_3$ | CH$_3$ | —CH$_2$N(CH$_3$)$_2$ | .C$_2$H$_2$O$_4$ mp. 210° C. |

TABLE 1-continued

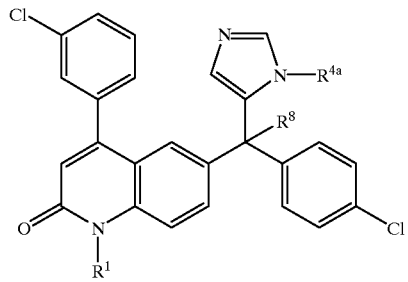

| Co. No. | Ex. No. | $R^1$ | $R^{4a}$ | $R^8$ | Physical data |
|---|---|---|---|---|---|
| 85 | B.4 | $CH_3$ | $CH_3$ | —$N(CH_3)_2$ | — |
| 86 | B.4 | $CH_3$ | $CH_3$ | $NHCOCH_2N(CH_3)_2$ | — |
| 87 | B.4 | $CH_3$ | $CH_3$ | —$NH(CH_2)_9CH_3$ | — |
| 88 | B.4 | $CH_3$ | $CH_3$ | —$NH(CH_2)_2NH_2$ | — |
| 89 | B.20 | $CH_3$ | $CH_3$ | —$NHCOCH_2OCH_3$ | .HCl mp. 220° C. |
| 90 | B.6 | $CH_3$ | $CH_3$ | H | — |
| 91 | B.20 | $CH_3$ | $CH_3$ | —$NHCOCH_2C_6H_5$ | .$C_2H_2O_4.H_2O$ mp. 170° C. |
| 92 | B.20 | $CH_3$ | $CH_3$ | —$NHCOC_6H_5$ | mp. 242° C. |
| 93 | B.20 | $CH_3$ | $CH_3$ | —$NHCOCONH_2$ | .$C_2H_2O_4.H_2O$ mp. 186° C. |
| 94 | B.13 | $CH_3$ | $CH_3$ | —$NHC_6H_5$ | mp. 165° C. |

\*: prepared by functional-group transformation of compound 70
\*\*: prepared by functional-group transformation of compound 25

TABLE 2

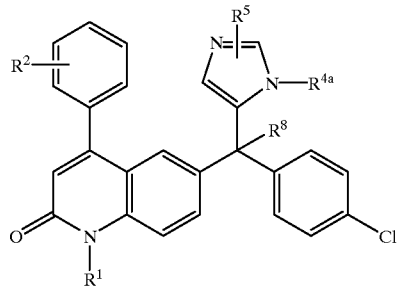

| Co. No. | Ex. No. | $R^1$ | $R^2$ | $R^{4a}$ | $R^5$ | $R^8$ | Physical data |
|---|---|---|---|---|---|---|---|
| 1 | B.1 | $CH_3$ | H | $CH_3$ | H | OH | mp. >250° C. |
| 2 | B.5 | $CH_3$ | H | $CH_3$ | H | H | mp. 100–110° C. |
| 26 | B.1 | $CH_3$ | 3-Cl | $CH_3$ | 2-$CH_3$ | OH | mp. 200° C. |
| 30 | B.6 | $CH_3$ | 3-Cl | $CH_3$ | 2-$CH_3$ | H | mp. 120–140° C.; .½($C_2H_2O_4$).$H_2O$ |
| 34 | B.1 | $CH_3$ | 3-O—$CH_2$—$CH_3$ | $CH_3$ | H | OH | mp. 190° C. |
| 35 | B.6 | $CH_3$ | 3-O—$CH_2$—$CH_3$ | $CH_3$ | H | H | mp. 160–180° C.; .HCl.$H_2O$ |
| 36 | B.1 | $CH_3$ | 3-O—$CH_3$ | $CH_3$ | H | OH | mp. 210° C. |
| 37 | B.1 | $CH_3$ | 3-O—$(CH_2)_2$—$CH_3$ | $CH_3$ | H | OH | mp. 150–160° C. |
| 38 | B.1 | $CH_3$ | 3-O—$(CH_2)_3$—$CH_3$ | $CH_3$ | H | OH | mp. 150–160° C. |
| 49 | B.1 | $CH_3$ | 4-O—$CH_2$—$CH_3$ | $CH_3$ | H | OH | mp. 184.2° C. |
| 50 | B.1 | $CH_3$ | 3-O—CH—$(CH_3)_2$ | $CH_3$ | H | OH | mp. 147.1° C. |
| 51 | B.6 | $CH_3$ | 3-O—$(CH_2)_3$—$CH_3$ | $CH_3$ | H | H | mp. 164.2° C.; .½($C_2H_2O_4$) |
| 52 | B.6 | $CH_3$ | 3-O—$(CH_2)_2$—$CH_3$ | $CH_3$ | H | H | .½($C_2H_2O_4$) |
| 53 | B.6 | $CH_3$ | 3-O—CH—$(CH_3)_2$ | $CH_3$ | H | H | mp. 133.9° C.; .$C_2H_2O_4.H_2O$ |

TABLE 2-continued

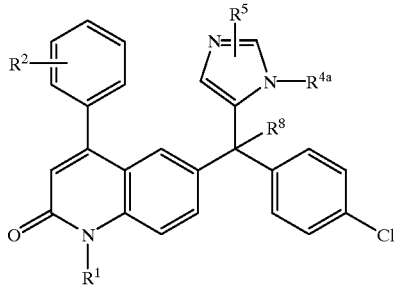

| Co. No. | Ex. No. | $R^1$ | $R^2$ | $R^{4a}$ | $R^5$ | $R^8$ | Physical data |
|---|---|---|---|---|---|---|---|
| 54 | B.14 | $CH_3$ | 3-OH | $CH_3$ | H | OH | — |
| 64 | B.10 | $CH_3$ | 3-OH | $CH_3$ | H | OH | .HCl.H$_2$O |
| 55 | B.6 | $CH_3$ | 3-OH | $CH_3$ | H | H | mp. >250° C. |
| 57 | B.1 | $CH_3$ | 2-OCH$_2$CH$_3$ | $CH_3$ | H | OH | — |
| 59 | B.13 | $CH_3$ | 3-OCH$_2$CH$_3$ | $CH_3$ | H | NH$_2$ | — |
| 95 | B.8a | $CH_3$ | 3-OCH$_2$CH$_3$ | $CH_3$ | H | NH$_2$ | (A) |
| 96 | B.8a | $CH_3$ | 3-OCH$_2$CH$_3$ | $CH_3$ | H | NH$_2$ | (B) |
| 62 | B.15 | $CH_3$ | 3-O(CH$_2$)$_2$N(CH$_3$)$_2$ | $CH_3$ | H | OH | — |
| 63 | B.11 | $CH_3$ | 3-O(CH$_2$)$_2$—OH | $CH_3$ | H | OH | — |
| 97 | B.1 | $CH_3$ | 3-CH$_2$CH$_3$ | $CH_3$ | H | OH | — |
| 98 | B.13 | $CH_3$ | 3-CH$_2$CH$_3$ | $CH_3$ | H | NH$_2$ | mp. 240° C. |
| 99 | B.1 | $CH_3$ | 3-(CH$_2$)$_2$CH$_3$ | $CH_3$ | H | OH | — |
| 100 | B.13 | $CH_3$ | 3-(CH$_2$)$_2$CH$_3$ | $CH_3$ | H | NH$_2$ | — |
| 101 | * | $CH_3$ | 3-O—(CH$_2$)$_2$OCH$_3$ | $CH_3$ | H | OH | .½(C$_2$H$_2$O$_4$) mp. 193° C. |
| 102 | B.1 | $CH_3$ | 3-CH$_3$ | $CH_3$ | H | OH | mp. >250° C. |
| 103 | B.13 | $CH_3$ | 3-CH$_3$ | $CH_3$ | H | NH$_2$ | — |
| 104 | B.1 | $CH_3$ | 3-Br | $CH_3$ | H | OH | — |
| 105 | B.13 | $CH_3$ | 3-Br | $CH_3$ | H | NH$_2$ | — |
| 106 | B.1 | $CH_3$ | 3-O—CF$_3$ | $CH_3$ | H | OH | — |
| 107 | B.13 | $CH_3$ | 3-O—CF$_3$ | $CH_3$ | H | NH$_2$ | mp. 168° C. |
| 108 | B.1 | $CH_3$ | 3-C$_6$H$_5$ | $CH_3$ | H | OH | — |
| 109 | B.13 | $CH_3$ | 3-C$_6$H$_5$ | $CH_3$ | H | NH$_2$ | — |
| 110 | B.1 | $CH_3$ | 3-F | $CH_3$ | H | OH | — |
| 111 | B.13 | $CH_3$ | 3-F | $CH_3$ | H | NH$_2$ | mp. >250° C. |
| 112 | B.1 | $CH_3$ | 3-(E)-CH=CH—CH$_3$ | $CH_3$ | H | OH | mp. >250° C. |
| 113 | B.2 | H | 3-Cl | $CH_3$ | 3-Cl | OH | — |
| 114 | B.4 | $CH_3$ | 3-Cl | $CH_3$ | 3-Cl | OH | — |
| 115 | B.1 | $CH_3$ | 3-Cl | H | 3-CH$_3$ | OH | — |
| 116 | B.4 | $CH_3$ | 3-Cl | $CH_3$ | 3-CH$_3$ | OH | — |
| 117 | ** | $CH_3$ | 3-CN | $CH_3$ | H | OH | — |
| 160 | B.1 | $CH_3$ | 3-CF$_3$ | $CH_3$ | H | OH | — |

*: prepared by functional-group transformation of compound 54
**: prepared by functional-group transformation of compound 104

TABLE 3

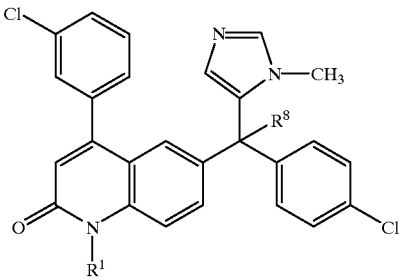

| Co. No. | Ex. No. | $R^1$ | $R^8$ | Physical data |
|---|---|---|---|---|
| 39 | B.4 | CH$_2$CONHCH(COOCH$_3$)(CH$_2$CH(CH$_3$)$_2$) | H | mp. 240° C.(S) |
| 40 | B.4 | CH$_2$-2-quinolinyl | H | mp. 240° C.; .2HCl |
| 41 | B.4 | CH$_2$CONHCH(COOCH$_3$)(CH$_2$CH(CH$_3$)$_2$) | OH | mp. >260° C.(S) |

TABLE 4
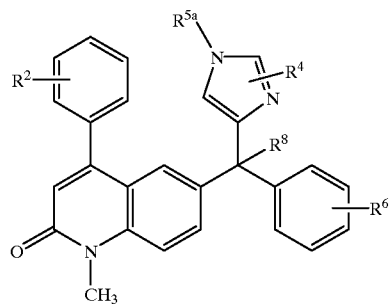
| Co. No. | Ex. No. | R² | R⁴ | R⁵ᵃ | R⁶ | R⁸ | Physical data |
|---|---|---|---|---|---|---|---|
| 42 | B.6 | H | H | H | 4-Cl | H | mp. 170° C.; .C₂H₂O₄.½H₂O |
| 43 | B.10 | H | H | H | 4-Cl | OH | mp. 180° C.; .H₂O |
| 44 | B.5 | H | H | CH₃ | 4-Cl | H | mp. 152° C. |
| 45 | B.6 | 3-Cl | H | H | 4-Cl | H | mp. 175° C.; .C₂H₂O₄ |
| 46 | B.5 | 3-Cl | H | CH₂CH₃ | 4-Cl | H | mp. 132° C.; .C₂H₂O₄ |
| 47 | B.5 | 3-Cl | H | CH₃ | 4-Cl | H | mp. 115° C.; .½C₂H₂O₄ |
| 48 | B.9 | 3-Cl | H | CH₃ | 4-Cl | OH | mp. 230° C. |
| 118 | B.4 | 3-Cl | 3-CH₃ | CH₃ | 4-Cl | OH | mp. 222° C. |
TABLE 5
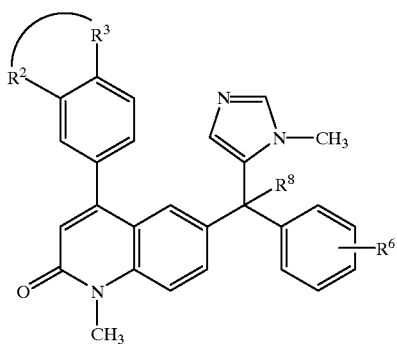
| Co. No. | Ex. No. | —R²—R³— | R⁶ | R⁸ |
|---|---|---|---|---|
| 119 | B.1 | —O—CH₂—O— | 4-Cl | OH |
| 120 | B.13 | —O—CH₂—O— | 4-Cl | NH₂ |
| 121 | B.1 | —O—CH₂—CH₂—O— | 4-Cl | OH |
| 122 | B.13 | —O—CH₂—CH₂—O— | 4-Cl | NH₂ |
| 123 | B.1 | —O—CH=CH— | 4-Cl | OH |

TABLE 6

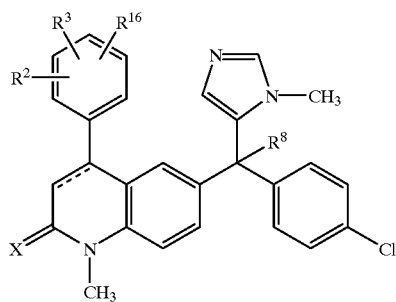

| Co. No. | Ex. No. | X | ==== | R² | R³ | R¹⁶ | R⁸ | Physical data |
|---|---|---|---|---|---|---|---|---|
| 124 | B.1 | O | double | 3-OCH₃ | 4-OCH₃ | 5-OCH₃ | OH | mp. 230° C. |
| 125 | B.13 | O | double | 3-OCH₃ | 4-OCH₃ | 5-OCH₃ | NH₂ | mp. 218° C. |
| 126 | B.1 | O | single | 3-Cl | H | H | OH | .C₂H₂O₄ mp. 160° C. |
| 127 | B.1 | O | single | 3-Cl | H | H | OH | — |
| 128 | B.16 | S | double | 3-Cl | H | H | H | — |

TABLE 7

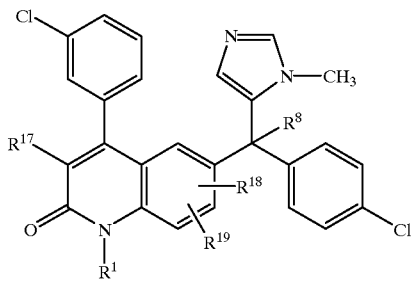

| Co. No. | Ex. No. | R¹ | R¹⁷ | R¹⁸ | R¹⁹ | R⁸ | Physical data |
|---|---|---|---|---|---|---|---|
| 129 | B.17 | H | CN | H | H | H | — |
| 130 | B.4 | CH₃ | CN | H | H | H | mp. 202° C. |
| 131 | B.17 | H | CN | H | H | OH | — |
| 132 | B.4 | CH₃ | CN | H | H | OH | — |
| 133 | B.17 | H | CN | H | H | —CH₂CN | — |
| 134 | B.4 | CH₃ | CN | H | H | —CH₂CN | mp. 138° C. |
| 135 | B.18 | H | CH₃ | H | H | OH | — |
| 136 | B.4 | CH₃ | CH₃ | H | H | OH | — |
| 137 | B.13 | CH₃ | CH₃ | H | H | NH₂ | mp. >250° C. |
| 138 | B.18 | H | C₆H₅ | H | H | H | — |
| 139 | B.4 | CH₃ | C₆H₅ | H | H | H | .½(C₂H₂O₄) mp. 180° C. |
| 140 | B.18 | H | C₆H₅ | H | H | OH | — |
| 141 | B.4 | CH₃ | C₆H₅ | H | H | OH | — |
| 142 | B.13 | CH₃ | C₆H₅ | H | H | NH₂ | — |
| 143 | B.13 | CH₃ | Cl | H | H | NH₂ | — |
| 144 | B.17 | H | —COOCH₂CH₃ | H | H | OH | — |
| 145 | B.4 | CH₃ | —COOCH₂CH₃ | H | H | OH | — |
| 146 | B.1 | CH₃ | H | 8-CH₃ | H | OH | — |
| 147 | B.13 | CH₃ | H | 8-CH₃ | H | NH₂ | .H₂O |
| 148 | B.1 | CH₃ | H | 7-Cl | H | OH | — |
| 149 | B.1 | CH₃ | H | 7-CH₃ | H | OH | — |
| 150 | B.1 | CH₃ | H | 5-CH₃ | H | OH | — |
| 151 | B.1 | CH₃ | H | 8-OCH₃ | H | OH | — |
| 161 | B.1 | CH₃ | H | 7-CH₃ | 8-CH₃ | OH | mp. 255° C. |

TABLE 8

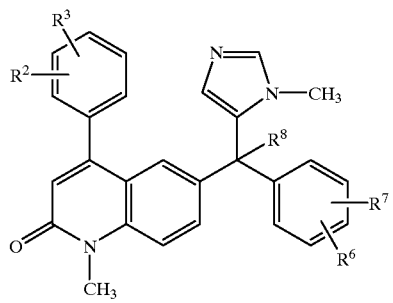

| Co. No. | Ex. No. | R² | R³ | R⁶ | R⁷ | R⁸ | Physical data |
|---|---|---|---|---|---|---|---|
| 152 | B.1 | 3-OCH₂CH₃ | H | 4-OCH₂CH₃ | H | OH | .3/2(C₂H₂O₄) |
| 153 | B.1 | 3-Cl | H | H | H | OH | — |
| 154 | B.1 | 3-Cl | H | 4-CH₃ | H | OH | — |
| 155 | B.1 | 3-Cl | H | 4-OCH₃ | H | OH | — |
| 156 | B.1 | 3-Cl | H | 4-CF₃ | H | OH | — |
| 157 | B.1 | 3-Cl | H | 2-Cl | 4-Cl | OH | — |
| 158 | B.1 | 3-Cl | 5-Cl | 4-Cl | H | OH | — |
| 159 | B.1 | 3-(4,4-dimethyl-oxazolin-2-yl) | H | 4-Cl | H | OH | — |
| 162 | B.1 | 3-Cl | H | 4-S—CH₃ | H | OH | mp. 169° C. .C₂H₂O₄.H₂O; |
| 163 | B.1 | 3-Cl | H | 4-N(CH₃)₂ | H | OH | mp. decomposes >172° C. |
| 164 | B.1 | 3-Cl | H | —CH=CH—CH=CH—* | | OH | .C₂H₂O₄ |

*R⁶ and R⁷ taken together to form a bivalent radical between positions 3 and 4 on the phenyl moiety

TABLE 9

| Comp. No. | Carbon Exp. | Carbon Theor. | Hydrogen Exp. | Hydrogen Theor. | Nitrogen Exp. | Nitrogen Theor. |
|---|---|---|---|---|---|---|
| 57 | 67.78 | 69.66 | 4.82 | 5.24 | 7.83 | 8.40 |
| 58 | 58.59 | 58.50 | 4.58 | 4.76 | 5.96 | 6.20 |
| 59 | 69.68 | 69.80 | 5.38 | 5.45 | 11.06 | 11.23 |
| 60 | 65.89 | 66.67 | 4.35 | 4.29 | 11.30 | 12.96 |
| 62 | 66.51 | 68.56 | 5.74 | 5.75 | 9.67 | 10.32 |
| 63 | 66.64 | 67.50 | 5.29 | 5.08 | 7.63 | 8.14 |
| 64 | 62.20 | 61.60 | 4.70 | 4.79 | 7.97 | 7.98 |
| 65 | 58.90 | 59.59 | 4.42 | 4.66 | 6.79 | 7.19 |
| 68 | 64.29 | 65.29 | 4.87 | 4.91 | 10.13 | 10.50 |
| 71 | 60.68 | 60.62 | 3.86 | 4.24 | 6.87 | 7.07 |
| 73 | 54.33 | 57.67 | 4.51 | 4.30 | 9.26 | 9.96 |
| 74 | 66.64 | 66.26 | 4.28 | 4.53 | 11.33 | 11.45 |
| 75 | 66.26 | 66.26 | 4.39 | 4.53 | 11.30 | 11.45 |
| 79 | 59.89 | 59.16 | 4.65 | 4.79 | 12.18 | 12.32 |
| 80 | 64.27 | 65.54 | 4.71 | 4.55 | 10.36 | 10.54 |
| 81 | 64.27 | 64.17 | 4.44 | 4.39 | 10.92 | 11.09 |
| 82 | 65.98 | 66.43 | 5.88 | 5.57 | 11.61 | 12.49 |
| 85 | 66.20 | 67.31 | 5.22 | 5.06 | 10.44 | 10.83 |
| 86 | 64.83 | 64.81 | 4.96 | 5.09 | 12.12 | 12.19 |
| 87 | 69.63 | 70.58 | 6.88 | 6.72 | 8.70 | 8.90 |
| 88 | 65.21 | 65.42 | 5.10 | 5.11 | 13.22 | 13.15 |
| 97 | 71.38 | 71.97 | 5.60 | 5.41 | 8.17 | 8.68 |
| 98 | 71.38 | 72.11 | 5.58 | 5.63 | 11.31 | 11.60 |
| 100 | 71.92 | 72.50 | 5.65 | 5.88 | 10.92 | 11.27 |
| 103 | 70.72 | 71.71 | 5.42 | 5.37 | 11.80 | 11.95 |
| 104 | 60.56 | 60.63 | 3.99 | 3.96 | 7.84 | 7.86 |
| 105 | 60.33 | 60.75 | 3.72 | 4.15 | 10.28 | 10.49 |
| 106 | 62.37 | 62.29 | 3.71 | 3.92 | 7.71 | 7.78 |
| 108 | 74.22 | 74.50 | 4.94 | 4.93 | 7.83 | 7.90 |
| 109 | 74.17 | 74.64 | 5.23 | 5.12 | 10.60 | 10.55 |
| 110 | 68.17 | 68.43 | 4.28 | 4.47 | 8.75 | 8.87 |
| 115 | 65.98 | 66.13 | 4.08 | 4.32 | 8.53 | 8.57 |
| 116 | 66.49 | 66.67 | 4.38 | 4.60 | 8.47 | 8.33 |
| 117 | 67.97 | 69.93 | 4.60 | 4.40 | 11.14 | 11.65 |
| 120 | 67.35 | 67.40 | 4.62 | 4.65 | 11.14 | 11.23 |
| 121 | 67.32 | 67.77 | 4.72 | 4.71 | 7.78 | 8.18 |
| 122 | 67.88 | 67.90 | 4.72 | 4.91 | 10.88 | 10.92 |
| 123 | 69.75 | 70.23 | 4.77 | 4.47 | 8.06 | 8.47 |
| 128 | 65.88 | 66.12 | 4.24 | 4.32 | 8.37 | 8.57 |
| 132 | 65.20 | 65.25 | 3.77 | 3.91 | 10.42 | 10.87 |
| 136 | 66.77 | 66.67 | 4.64 | 4.60 | 8.34 | 8.33 |
| 142 | 69.26 | 70.09 | 4.42 | 4.63 | 9.59 | 9.91 |
| 145 | 64.36 | 64.06 | 4.19 | 4.48 | 7.49 | 7.47 |
| 148 | 61.88 | 61.79 | 3.65 | 3.84 | 7.88 | 8.01 |
| 150 | 66.56 | 66.67 | 4.64 | 4.60 | 8.08 | 8.33 |
| 151 | 64.76 | 64.62 | 4.86 | 4.45 | 7.80 | 8.07 |
| 153 | 70.99 | 71.13 | 5.17 | 4.86 | 9.25 | 9.22 |
| 154 | 71.67 | 71.56 | 5.08 | 5.15 | 9.14 | 8.94 |
| 158 | 61.72 | 61.79 | 3.76 | 3.84 | 7.96 | 8.01 |
| 159 | 69.28 | 69.50 | 5.21 | 5.29 | 10.01 | 10.13 |
| 160 | 62.71 | 64.19 | 3.91 | 4.04 | 7.36 | 8.02 |

C. Pharmacological Example

C.1. Inhibition of smooth muscle cell proliferation.

The effects of the compounds of the present invention were studied in human pulmonary artery smooth muscle cells (PASMC), human coronary artery smooth muscle cells (CASMC), and rat A10 arterial smooth muscle cells growing under standard tissue culture conditions. CASMC and PASMC cell cultures were purchased from Clonetics (San Diego, Calif.). A10 smooth muscle cells were purchased from the American Type Culture Collection (Bethesda, Md.). Cells were inoculated at an initial cell density of 50,000 cells per well in six-well plastic cluster tissue culture dishes in 3.0 ml of complete growth medium. Test compounds were dissolved in dimethylsulfoxide (DMSO) and added in a 3 μl volume to each well to produce the desired concentrations of said test compound (5, 10, 50, 100 and 500 nM final concentrations). Cells were incubated for six days. On day 4, fresh medium plus a fresh solution containing the test compound were added to the cell cultures. On day 6, the growth medium was removed by aspiration. The cells were detached by trypsinizing in 1.0 ml of trypsin-EDTA solution. The cell suspensions were transferred to 20 ml of an isotonic diluent and 0.5 ml of the diluted cell suspension was counted with a Coulter particle counter. Cell counts from test compound-treated cultures were normalized to cell counts obtained from DMSO-treated controls and expressed as percent inhibition. $IC_{50}$ values (concentration of test compound producing a 50% inhibition of cell proliferation) were derived from the inhibition data. These results are summarized in Table C.1.

TABLE C.1

Inhibition of Smooth Muscle Cell Proliferation

| Cell Line | $IC_{50}$ (nM) Co. No. 75 |
|---|---|
| A10 | 14 |
| PASMC | 24 |
| CASMC | 16 |

What is claimed is:

1. A method for treating a condition associated with smooth muscle cell proliferation in a warm-blooded animal which comprises administering to said warm-blooded animal a prophylactically or therapeutically effective amount of a compound of formula (I),

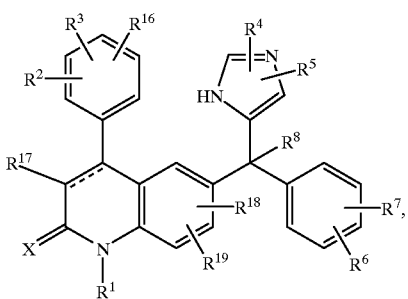

(I)

a stereoisomeric form thereof, a pharmaceutically acceptable acid or base addition salt thereof, wherein
the dotted line represents an optional bond;
X is oxygen or sulfur;
$R^1$ is hydrogen, $C_{1-12}$alkyl, $Ar^1$, $Ar^2C_{1-6}$alkyl, quinolinylC$_{1-6}$alkyl, pyridylC$_{1-6}$alkyl, hydroxyC$_{1-6}$ alkyl, $C_{1-6}$alkyloxyC$_{1-6}$alkyl, mono- or di($C_{1-6}$alkyl) aminoC$_{1-6}$alkyl, aminoC$_{1-6}$alkyl,
or a radical of formula —Alk$^1$—C(=O)—R$^9$, —Alk$^1$—S(O)—R$^9$ or —Alk$^1$—S(O)$_2$—R$^9$,
wherein Alk$^1$ is $C_{1-6}$alkanediyl,
$R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;
$R^2$, $R^3$ and $R^{16}$ each independently are hydrogen, hydroxy, halo, cyano, $C_{1-6}$alkyl, $C_{1-6}$alkyloxy, hydroxyC$_{1-6}$alkyloxy, $C_{1-6}$alkyloxyC$_{1-6}$alkyloxy, aminoC$_{1-6}$alkyloxy, mono- or di($C_{1-6}$alkyl)aminoC$_{1-6}$ alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl, 4,4-dimethyloxazolyl; or
when on adjacent positions $R^2$ and $R^3$ taken together may form a bivalent radical of formula

| —O—CH$_2$—O— | (a-1), |
| —O—CH$_2$—CH$_2$—O— | (a-2), |
| —O—CH=CH— | (a-3), |
| —O—CH$_2$—CH$_2$— | (a-4), |
| —O—CH$_2$—CH$_2$—CH$_2$— | (a-5), or |
| —CH=CH—CH=CH— | (a-6); |

$R^4$ and $R^5$ each independently are hydrogen, halo, $Ar^1$, $C_{1-6}$alkyl, hydroxyC$_{1-6}$alkyl, $C_{1-6}$alkyloxyC$_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)C$_{1-6}$alkyl or $C_{1-6}$alkylS(O)$_2$C$_{1-6}$alkyl;
$R^6$ and $R^7$ each independently are hydrogen, halo, cyano, $C_{1-6}$alkyl, $C_{1-6}$alkyloxy, $Ar^2$oxy, trihalomethyl, $C_{1-6}$alkylthio, di($C_{1-6}$alkyl)amino, or
when on adjacent positions $R^6$ and $R^7$ taken together may form a bivalent radical of formula

| —O—CH$_2$—O— | (c-1), or |
| —CH=CH—CH=CH— | (c-2); |

$R^8$ is hydrogen, $C_{1-6}$alkyl, cyano, hydroxycarbonyl, $C_{1-6}$alkyloxycarbonyl, $C_{1-6}$alkylcarbonylC$_{1-6}$alkyl, cyanoC$_{1-6}$alkyl, $C_{1-6}$alkyloxycarbonylC$_{1-6}$alkyl, carboxyC$_{1-6}$alkyl, hydroxyC$_{1-6}$alkyl, aminoC$_{1-6}$alkyl, mono- or di($C_{1-6}$alkyl)aminoC$_{1-6}$alkyl, imidazolyl, haloC$_{1-6}$alkyl, $C_{1-6}$alkyloxyC$_{1-6}$alkyl, aminocarbonylC$_{1-6}$alkyl, or a radical of formula

| —O—R$^{10}$ | (b-1), |
| —S—R$^{10}$ | (b-2), |
| —N—R$^{11}$R$^{12}$ | (b-3), | wherein $R^{10}$ is hydrogen, $C_{1-6}$alkyl, $C_{1-6}$alkylcarbonyl, $Ar^1$, $Ar^2C_{1-6}$alkyl, $C_{1-6}$alkyloxycarbonylC$_{1-6}$alkyl, a radical or formula —Alk$^2$—OR$^{13}$ or —Alk$^2$—NR$^{14}$R$^{15}$;
$R^{11}$ is hydrogen, $C_{1-12}$alkyl, $Ar^1$ or $Ar^2C_{1-6}$alkyl;
$R^{12}$ is hydrogen, $C_{1-6}$alkyl, $C_{1-16}$alkylcarbonyl, $C_{1-6}$alkyloxycarbonyl, $C_{1-6}$alkylaminocarbonyl, $Ar^1$, Ar$^2$C$_{1-6}$alkyl, C$_{1-6}$alkylcarbonylC$_{1-6}$alkyl, a natural amino acid, Ar$^1$carbonyl, Ar$^2$C$_{1-6}$alkylcarbonyl, aminocarbonylcarbonyl, C$_{1-6}$alkyloxyC$_{1-6}$alkylcarbonyl, hydroxy, C$_{1-6}$alkyloxy, aminocarbonyl, di(C$_{1-6}$alkyl)aminoC$_{1-6}$alkylcarbonyl, amino, C$_{1-6}$alkylamino, C$_{1-6}$alkylcarbonylamino, or a radical of formula —Alk$^2$—OR$^{13}$ or —Alk$^2$—NR$^{14}$R$^{15}$;

wherein Alk$^2$ is C$_{1-6}$alkanediyl;

R$^{13}$ is hydrogen, C$_{1-6}$alkyl, C$_{1-6}$alkylcarbonyl, hydroxyC$_{1-6}$alkyl, Ar$^1$ or Ar$^2$C$_{1-6}$alkyl;

R$^{14}$ is hydrogen, C$_{1-6}$alkyl, Ar$^1$ or Ar$^2$C$_{1-6}$alkyl;

R$^{15}$ is hydrogen, C$_{1-6}$alkyl, C$_{1-6}$alkylcarbonyl, Ar$^1$ or Ar$^2$C$_{1-6}$alkyl;

R$^{17}$ is hydrogen, halo, cyano, C$_{1-6}$alkyl, C$_{1-6}$alkyloxycarbonyl, Ar$^1$;

R$^{18}$ is hydrogen, C$_{1-6}$alkyl, C$_{1-6}$alkyloxy or halo;

R$^{19}$ is hydrogen or C$_{1-6}$alkyl;

Ar$^1$ is phenyl or phenyl substituted with C$_{1-6}$alkyl, hydroxy, amino, C$_{1-6}$alkyloxy or halo; and Ar$^2$ is phenyl or phenyl substituted with C$_{1-6}$alkyl, hydroxy, amino, C$_{1-6}$alkyloxy or halo.

2. A method according to claim 1 wherein X is oxygen, the dotted line represents a bond and R$^1$ is hydrogen, C$_{1-6}$alkyl, C$_{1-6}$alkyloxyC$_{1-6}$alkyl or mono- or di(C$_{1-6}$alkyl)aminoC$_{1-6}$alkyl.

3. A method according to claim 1 wherein R$^3$ is hydrogen and R$^2$ is halo, C$_{1-6}$alkyl, C$_{2-6}$alkenyl, C$_{1-6}$alkyloxy, trihalomethoxy or hydroxyC$_{1-6}$alkyloxy.

4. A method according to claim 1 wherein R$^8$ is hydrogen, hydroxy, haloC$_{1-6}$alkyl, hydroxyC$_{1-6}$alkyl, cyanoC$_{1-6}$alkyl, C$_{1-6}$alkyloxycarbonylC$_{1-6}$alkyl, imidazolyl, or a radical of formula —NR$^{11}$R$^{12}$ wherein R$^{11}$ is hydrogen or C$_{1-12}$alkyl and R$^{12}$ is hydrogen, C$_{1-6}$alkyl, C$_{1-6}$alkyloxy, C$_{1-6}$alkyloxyC$_{1-6}$alkylcarbonyl, hydroxy, or a radical of formula —Alk$^2$—OR$^{13}$ wherein R$^{13}$ is hydrogen or C$_{1-6}$alkyl.

5. A method according to claim 1 wherein the compound is (+)-6-[amino(4-chlorophenyl)(1-methyl-1H-imidazol-5-yl)methyl]-4-(3-chlorophenyl)-1-methyl-2(1H)-quinolinone; or a pharmaceutically acceptable acid addition salt thereof.

6. A method according to claim 1 wherein said condition is atherosclerosis.

7. A method according to claim 1 wherein said condition is restenosis.

8. A method according to claim 1 wherein said condition is percutaneous transluminal coronary angioplasty restenosis or coronary artery stent restenosis.

* * * * *